United States Patent
Min et al.

(10) Patent No.: US 11,191,880 B2
(45) Date of Patent: *Dec. 7, 2021

(54) FILL AND FINISH SYSTEMS AND METHODS FOR SMALL VOLUME PROCESSING

(71) Applicant: Fenwal, Inc., Lake Zurich, IL (US)

(72) Inventors: Kyungyoon Min, Kildeer, IL (US); Christopher J. Wegener, Libertyville, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,347

(22) Filed: May 14, 2019

(65) Prior Publication Data

US 2019/0351113 A1 Nov. 21, 2019

Related U.S. Application Data

(60) Provisional application No. 62/672,236, filed on May 16, 2018.

(51) Int. Cl.
*A61M 1/02* (2006.01)
*B01D 63/16* (2006.01)

(52) U.S. Cl.
CPC ........... *A61M 1/0281* (2013.01); *B01D 63/16* (2013.01); *A61M 2205/128* (2013.01);
(Continued)

(58) Field of Classification Search
CPC ........ A61M 1/0281; A61M 1/00; A61M 1/02; A61M 1/26; A61M 1/34; A61M 1/36;
(Continued)

(56) References Cited

U.S. PATENT DOCUMENTS 5,789,147 A 8/1998 Rubinstein et al.
5,840,502 A 11/1998 Van Vlasselaer
(Continued)

FOREIGN PATENT DOCUMENTS

EP 1254675 11/2002
EP 3192541 7/2019
(Continued)

OTHER PUBLICATIONS

European Patent Office, extended European Search Report, counterpart EP Appl. No. 19174670, dated Oct. 9, 2019.

*Primary Examiner* — Robert Clemente
*Assistant Examiner* — Akash K Varma
(74) *Attorney, Agent, or Firm* — Cook Alex Ltd.

(57) ABSTRACT

A system for processing fluids and filling a container with a product includes a disposable fluid circuit and reusable hardware configured to accept the disposable fluid circuit. The disposable fluid circuit includes a spinning membrane separator, first and second syringes, and a flow control cassette. The reusable hardware includes a drive coupled to the spinning membrane separator, first and second syringe pumps, the first and second syringes coupled to the first and second syringe pumps respectively, and a controller. The system also includes a syringe pump for filling low-volume containers, which syringe pump may be one of the first and second syringe pumps, or may be a third syringe pump. The syringe pump for filling low-volume containers may include a filtered vacuum/pressure source and a position detector.

15 Claims, 23 Drawing Sheets

(52) U.S. Cl.
CPC .... *B01D 2313/18* (2013.01); *B01D 2313/243* (2013.01); *B01D 2313/50* (2013.01)

(58) Field of Classification Search
CPC .... A61M 1/38; A61M 1/0068; A61M 1/0209; A61M 1/0272; A61M 1/262; A61M 2205/128; B01D 63/16; B01D 2313/243; B01D 2313/50; B01D 2313/18
USPC ........................................................ 210/104
See application file for complete search history.

(56) References Cited

U.S. PATENT DOCUMENTS

| | | | |
|---|---|---|---|
| 6,464,624 B2 | 10/2002 | Pages | |
| 6,709,378 B2 | 3/2004 | Nishimura et al. | |
| 6,716,151 B2 | 4/2004 | Panzani et al. | |
| 6,733,433 B1 * | 5/2004 | Fell | A61M 1/3693 435/2 |
| 7,011,852 B2 | 3/2006 | Sukavaneshvar et al. | |
| 7,179,391 B2 | 2/2007 | Leach et al. | |
| 7,291,450 B2 | 11/2007 | Sowemimo-Coker et al. | |
| 7,364,657 B2 | 4/2008 | Mandrusov et al. | |
| 7,374,678 B2 | 5/2008 | Leach et al. | |
| 8,101,077 B2 | 1/2012 | Sukavaneshvar et al. | |
| 8,439,889 B2 | 5/2013 | Sano | |
| 8,808,551 B2 | 8/2014 | Leach et al. | |
| 8,961,787 B2 | 2/2015 | Wood et al. | |
| 8,986,185 B2 | 3/2015 | Del Vecchio | |
| 9,352,021 B2 | 5/2016 | Hanna et al. | |
| 9,452,254 B2 | 9/2016 | Kimura et al. | |
| 9,459,186 B2 | 10/2016 | Mastromatteo et al. | |
| 9,603,986 B2 | 3/2017 | Kusters et al. | |
| 9,717,842 B2 | 8/2017 | Min et al. | |
| 9,907,899 B2 | 3/2018 | Kim | |
| 10,329,530 B2 | 6/2019 | Wegener | |
| 2002/0128583 A1 * | 9/2002 | Min | A61M 1/3687 604/6.01 |
| 2008/0171951 A1 | 7/2008 | Fell | |
| 2011/0124106 A1 | 5/2011 | Froman et al. | |
| 2013/0092630 A1 | 4/2013 | Wegener | |
| 2013/0341291 A1 | 12/2013 | Wegener et al. | |
| 2014/0199680 A1 | 7/2014 | Min et al. | |
| 2015/0080204 A1 | 3/2015 | Kassis | |
| 2015/0101707 A1 | 4/2015 | Ranalletta et al. | |
| 2016/0252434 A1 | 9/2016 | Smith et al. | |
| 2018/0015418 A1 | 1/2018 | Binninger et al. | |
| 2018/0155070 A1 | 6/2018 | Min et al. | |

FOREIGN PATENT DOCUMENTS

| | | | |
|---|---|---|---|
| WO | WO 2018/065880 | 4/2018 | |
| WO | WO-2018065880 A1 * | 4/2018 | .......... A61M 5/2053 |

* cited by examiner

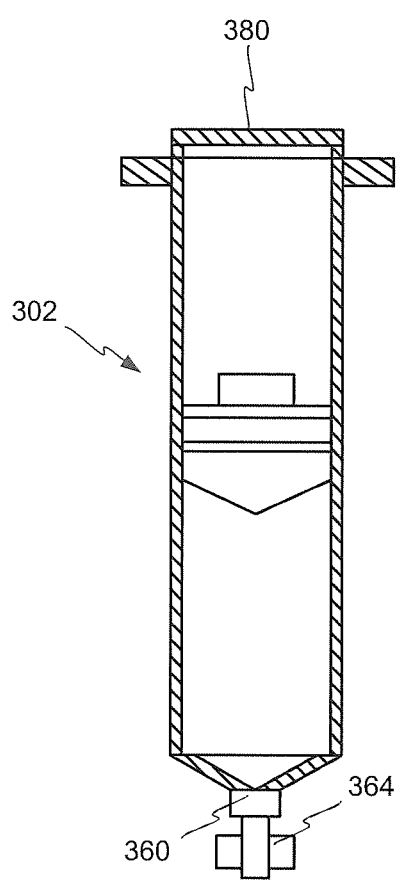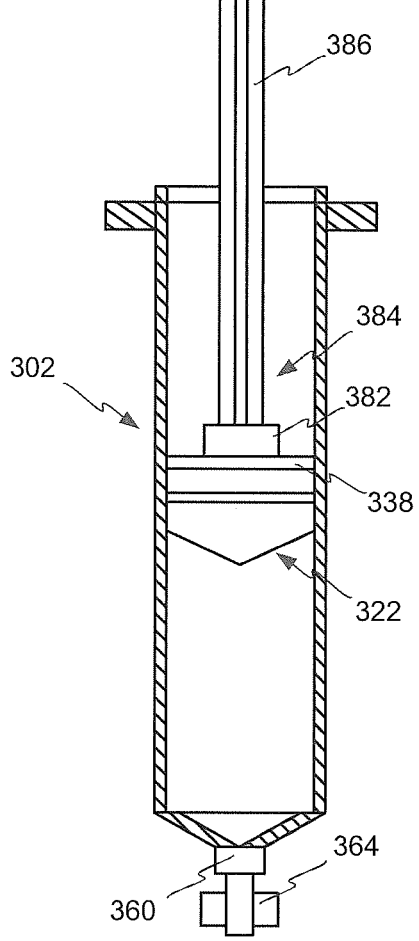
*Fig. 29*     *Fig. 30*

FILL AND FINISH SYSTEMS AND METHODS FOR SMALL VOLUME PROCESSING

CROSS-REFERENCE TO RELATED APPLICATIONS

This application claims the benefit of U.S. Provisional Patent App. No. 62/672,236, filed May 16, 2018, which is expressly incorporated herein by reference in its entirety.

TECHNICAL FIELD

The present disclosure is generally directed to systems and methods for processing (e.g., washing) suspensions of cells, and then filling the cell suspension into one or more containers. More particularly, the present disclosure is directed to systems and methods for processing small volumes of cells using a disposable fluid circuit and a reusable processing machine or hardware to generate a cell product, and for filling the cell product into one or more containers, including end-user (such as single-use) containers.

BACKGROUND

A number of well-known therapies are currently practiced in which a targeted cellular blood component (e.g., red blood cells, white blood cells, and platelets) is separated from whole blood and stored for later infusion to a patient. The targeted cell product (e.g., red blood cells or platelets) may be in a suspension that includes plasma and/or some other supernatant. As such, it is sometimes desirable to "wash" the cellular suspension (typically with saline) to remove the plasma/supernatant, as well as any non-target cellular material, prior to reinfusion.

Systems and methods for cell washing are exemplified by US Pub. Nos. 2013/0341291, 2013/0092630, and 2014/0199680, each of which is incorporated herein by reference. Each of these published applications discloses cell washing methods utilizing disposable fluid circuits including a spinning membrane separator and a reusable processing machine. Such machines include peristaltic pumps and pinch valves that act on the tubing of the fluid circuit to direct flow within the fluid circuit.

The fluid circuits in the published applications listed above have a relatively large internal volume, and thus require relatively large volumes of wash or flush media to clear processed fluid through the fluid circuit. While such systems and fluid circuits are capable of washing and reducing the volume of the targeted cell component into final volumes of ranging from approximately 50 mL to 5,000 mL, there are instances in which smaller final volumes (e.g., 10 mL) are desired, such as when processing single-dose quantities of mononuclear cell products. Thus, it would be desirable to provide systems and methods for processing (e.g., washing) small volumes of cellular suspensions.

Moreover, when the processing is complete using the large volume systems described above, the product typically is directed into a product container, such as a flexible walled bag, because of the large volumes of cell product involved. At the time of use, the product may be removed from the bag via a port or port assembly. In particular, one or more syringes may be connected to the port, and then the product from the bag is drawn into the syringe. Despite the user's best efforts, cells may be left in the product bag and not transferred to the syringes. Further, the method provides the potential for contamination of the product in the syringe if proper sterilization protocols are not used.

If a machine and fluid circuit were designed to permit processing of small volumes of cellular suspensions, however, then the storage of the resultant cell product in a large volume container with subsequent filling of the cell product into small volume container(s) for delivery to the patient may be reduced or avoided. That is, if it were possible to provide a machine and fluid circuit for processing small volumes of cell suspension, then it further would be desirable to direct these small volumes directly into one or more small volume delivery containers without the need to use an intermediate large volume container for storage.

SUMMARY

In a first aspect, a system for processing fluids and filling a container with a product includes a disposable fluid circuit and reusable hardware configured to accept the disposable fluid circuit. The disposable fluid circuit includes a spinning membrane separator having an inlet, a retentate outlet, and a filtrate outlet, a filtrate container, a wash medium container, first and second syringes, and a flow control cassette. The flow control cassette includes a housing, (i) a first fluid pathway with a first inlet configured to be in fluid communication with a source container, a second inlet in fluid communication with the wash medium container, and an outlet in fluid communication with the inlet of the spinning membrane separator, (ii) a second fluid pathway with an inlet in fluid communication with the retentate outlet, a first outlet, and a second outlet in fluid communication with the first syringe, (iii) a third fluid pathway with an inlet in fluid communication with the filtrate outlet, a first outlet in fluid communication with the filtrate container, and a second outlet in fluid communication with the second syringe, and at least one valve associated with each of the first, second and third fluid pathways. The reusable hardware includes a drive coupled to the spinning membrane separator, first and second syringe pumps, the first and second syringes coupled to the first and second syringe pumps respectively, the first syringe pump configured to move a plunger within the first syringe and the second syringe pump configured to move a plunger within the second syringe, a third syringe pump with a third syringe having a barrel and a plunger moveable along the barrel between a first end coupled to the first outlet of the second fluid flow path and a second end, the second end being coupled to a vacuum/pressure source with a filter disposed between the second end and the vacuum/pressure source, and the third syringe pump including a position detector to determine the position of the plunger along the barrel of the third syringe; and at least one controller coupled to the flow control cassette, the drive, and the first, second, and third syringe pumps, and configured to selectively operate the flow control cassette, the drive and the first, second, and third syringe pumps. The at least one controller is configured to operate the vacuum/pressure source to cause or permit the plunger of the third syringe to move to receive a cell product into the barrel of the third syringe In a second aspect, a system for processing fluids and filling a container with a product includes a disposable fluid circuit and reusable hardware configured to accept the disposable fluid circuit. The disposable fluid circuit includes a spinning membrane separator having an inlet, a retentate outlet, and a filtrate outlet, a filtrate container, a wash medium container, first and second syringes, and a flow control cassette. The flow control cassette includes a housing, (i) a first fluid pathway with a first inlet configured to be in fluid communication with a source container, a second inlet in fluid communication with the wash medium container, and an outlet in fluid communication with the inlet of the spinning membrane separator, (ii) a second fluid pathway with an inlet in fluid communication with the retentate outlet, a first outlet, and a second outlet in fluid communication with the first syringe, (iii) a third fluid pathway with an inlet in fluid communication with the filtrate outlet, a first outlet in fluid communication with the filtrate container, and a second outlet in fluid communication with the second syringe, and at least one valve associated with each of the first, second and third fluid pathways. The reusable hardware includes a drive coupled to the spinning membrane separator, first and second syringe pumps, the first and second syringes coupled to the first and second syringe pumps respectively, the first syringe pump configured to move a plunger within the first syringe and the second syringe pump configured to move a plunger within the second syringe, the first syringe having a barrel and a first plunger moveable along the barrel between a first end coupled to the second outlet of the second fluid flow path and a second end, the second end being coupled to a vacuum/pressure source with a filter disposed between the second end and the vacuum/pressure source, and the first syringe pump including a position detector to determine the position of the first plunger along the barrel, and a controller coupled to the flow control cassette, the drive, and the first and second syringe pumps, and configured to selectively operate the flow control cassette, the drive and the first and second syringe pumps. The controller is configured to operate the vacuum/pressure source to move the first plunger to draw a cell product into the barrel and to deliver the cell product from the barrel to a container in fluid communication with the first outlet of the second fluid pathway, the container comprising a low-volume container.

In a third aspect, A system for processing fluids and filling a container with a product includes a disposable fluid circuit and reusable hardware configured to accept the disposable fluid circuit. The disposable fluid circuit includes a spinning membrane separator having an inlet, a retentate outlet, and a filtrate outlet, a filtrate container, a wash medium container, first and second syringes, and a flow control cassette. The flow control cassette includes a housing, (i) a first fluid pathway with a first inlet configured to be in fluid communication with a source container, a second inlet in fluid communication with the wash medium container, and an outlet in fluid communication with the inlet of the spinning membrane separator, (ii) a second fluid pathway with an inlet in fluid communication with the retentate outlet and an outlet in fluid communication with the first syringe, (iii) a third fluid pathway with an inlet in fluid communication with the filtrate outlet, a first outlet in fluid communication with the filtrate container, and a second outlet in fluid communication with the second syringe, and at least one valve associated with each of the first, second and third fluid pathways. The reusable hardware includes a drive coupled to the spinning membrane separator, first and second syringe pumps, the first and second syringes coupled to the first and second syringe pumps respectively, the first syringe pump configured to move a plunger within the first syringe and the second syringe pump configured to move a plunger within the second syringe, the first syringe having a barrel and a first plunger moveable along the barrel between a first end coupled to the outlet of the second fluid flow path and a second end, the second end being coupled to a vacuum/pressure source with a filter disposed between the second end and the vacuum/pressure source, and the first syringe pump including a position detector to determine the position of the first plunger along the barrel, and a controller coupled to the flow control cassette, the drive, and the first and second syringe pumps, and configured to selectively operate the flow control cassette, the drive and the first and second syringe pumps. The controller is configured to operate the vacuum/pressure source to move the first plunger to draw a cell product into the barrel, the first syringe being detachable from the first syringe pump and the outlet of the second fluid pathway.

DESCRIPTION OF THE DRAWINGS

FIG. 29 is a cross-sectional view of a pre-filled syringe produced using the embodiment of FIG. 22.

FIG. 30 is a cross-sectional view of the pre-filled syringe of FIG. 29 configured for administration to a patient.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
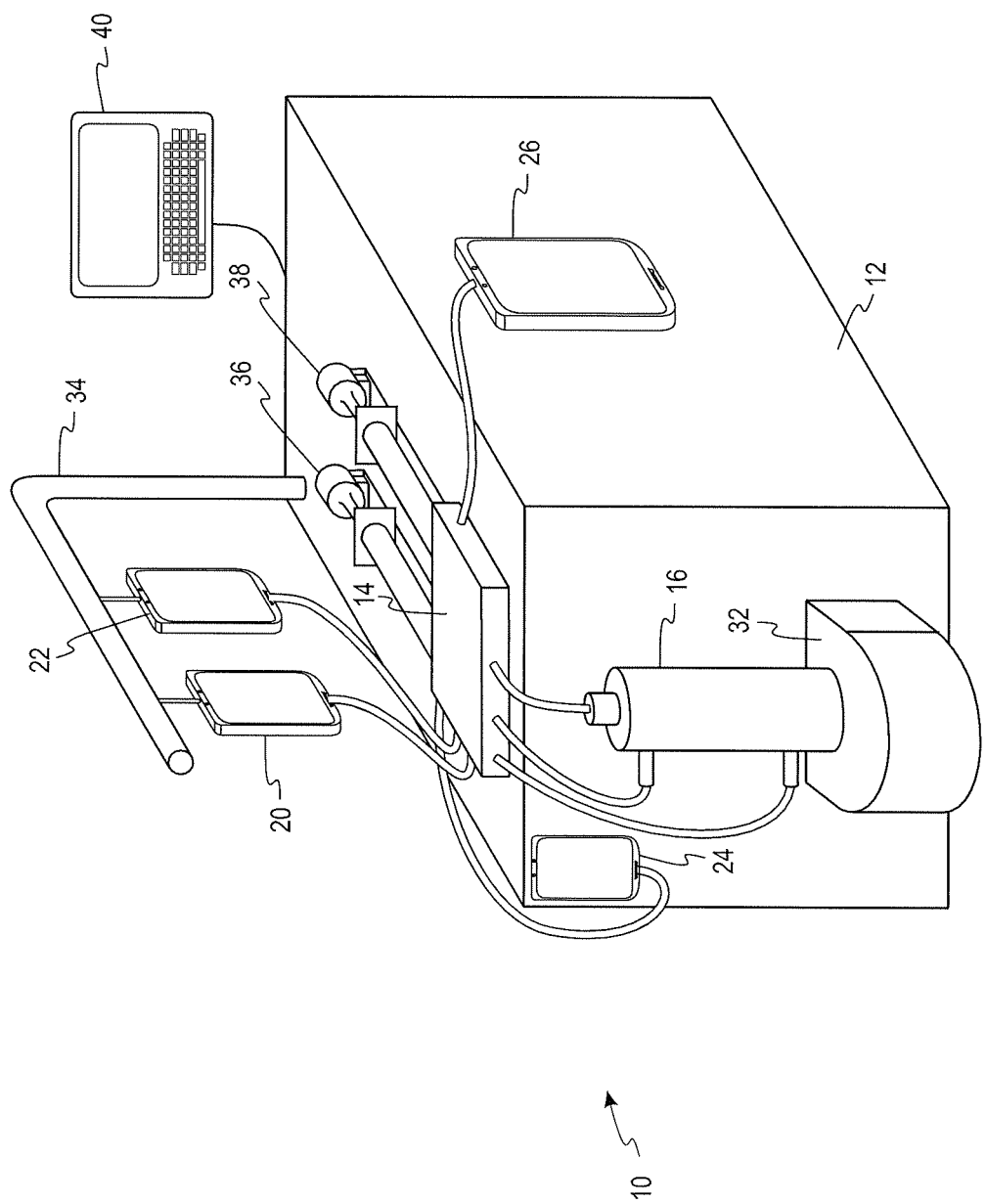
FIG. 1 is a perspective view of a system for processing (e.g., washing) small volumes of cellular suspensions including a reusable machine and a disposable fluid circuit, or kit.

Turning first to FIG. 1, an embodiment of a system 10 for processing cell suspensions (e.g., cell washing) is illustrated, the system 10 including a reusable hardware component 12 and a disposable kit component (also referred to as a fluid circuit or set) 14.

Figure 2:
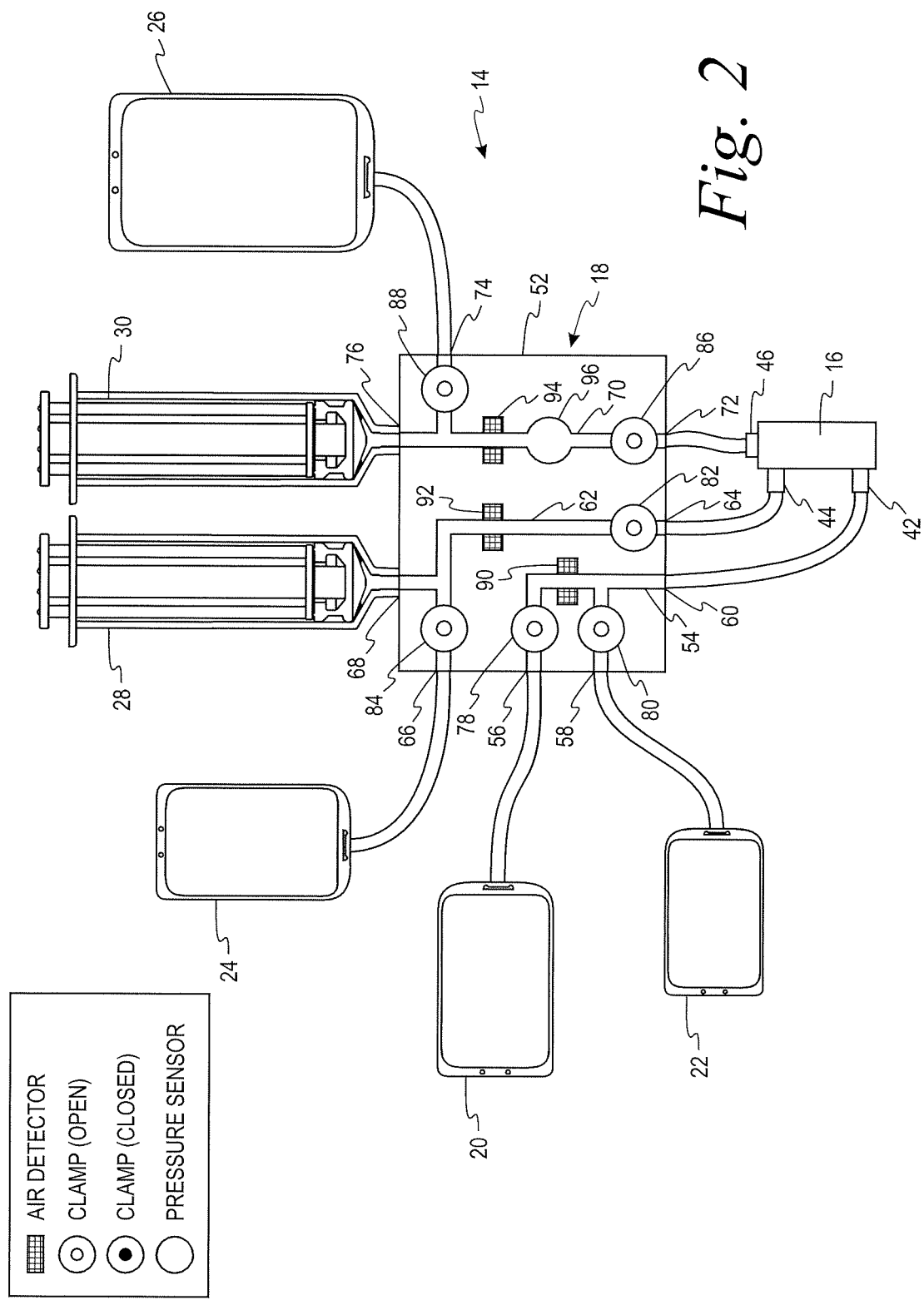
FIG. 2 is a schematic view of the disposable kit for use in the system of FIG. 1.

As seen in FIG. 2, the disposable kit 14 includes a spinning membrane separator 16 (such as is well known in the art), a cassette 18 for providing fluid management through the kit, and various containers 20, 22, 24, 26 and syringes 28, 30 (each comprising a body or barrel portion and a plunger) in fluid communication with the cassette 18. Tubings interconnect each of the various containers 20, 22, 24, 26, as well as the inlet and outlets of the spinning membrane separator 16, to the cassette 18. Preferably the length of each of the interconnecting tubings is kept as short as possible to further minimize the internal volume of the kit 14. Also, it is preferable that discharge ports of the syringes 28, 30 be configured to be removably connected directly to the cassette 18, again to minimize the internal volume of the kit. Alternatively, the syringes 28, 30 and/or the spinning membrane separator 16 may be integrally formed as part of the cassette 18, so as to be internal to the cassette housing and further reduce the tubing volume associated with the kit 14.

Returning to FIG. 1, the reusable hardware component 12 includes a drive system/support 32 for the spinning membrane separator 16, supports 34 for the various containers of the disposable kit, a syringe pump 36, 38 for each syringe 28, 30, and a controller 40 for automatically controlling operation of the system. The controller 40 may include a microprocessor (which, in fact may include multiple physical and/or virtual processors). According to other embodiments, the controller 40 may include one or more electrical circuits designed to carry out the actions described herein. In fact, the controller 40 may include a microprocessor and other circuits or circuitry. In addition, the controller 40 may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described below.

Specifically, the disposable kit 14 comprises a spinning membrane separator 16 having an inlet 42 for flowing the suspension of cellular material to be washed and a wash medium into the spinning membrane separator, a first outlet 44 for flowing retentate comprising washed cells from the spinning membrane separator, and a second outlet 46 for flowing filtrate comprising a non-cellular component of the cellular suspension and wash medium from the spinning membrane separator.

Figure 3:
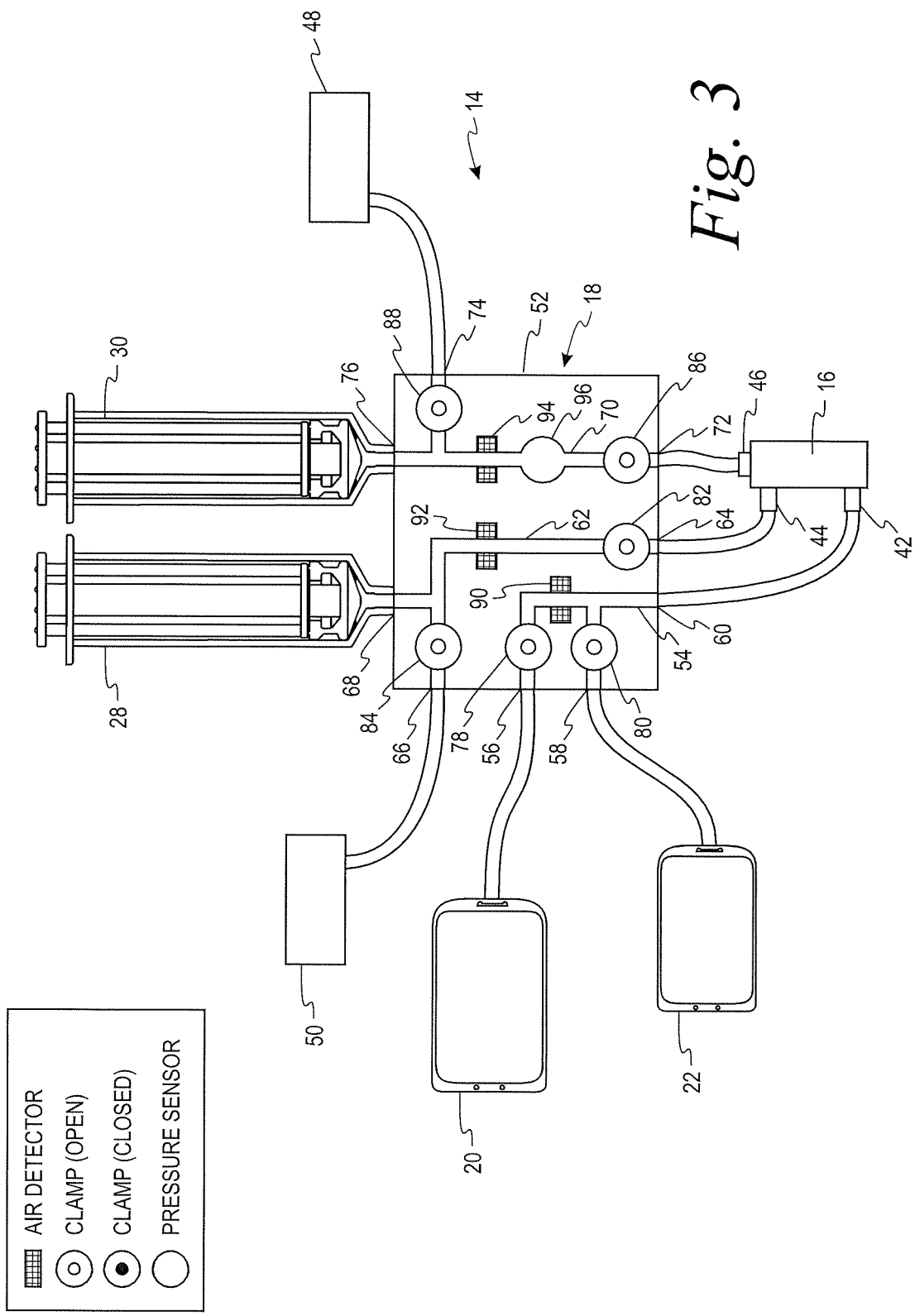
FIG. 3 is a schematic view of an alternate configuration of the disposable kit of FIG. 2.

The kit further includes containers 24, 26 for receiving the retentate and the filtrate, respectively, and also either includes a container 22 of wash medium integrally connected to the kit at the time of manufacture or is configured to be connected to a container of wash medium at the point of use. Alternatively, with reference to FIG. 3, a sterile vent 48, 50 can replace each of the containers 24, 26 for receiving the retentate and the filtrate.

Fluid management of the kit 14 is controlled by the cassette 18, which cassette 18 may also be referred to as a fluid management system. The cassette 18 comprises a housing 52 having a series of fluid pathways therein interconnecting the various other components of the disposable kit 14, each of the fluid pathways having flow control mechanisms associated therewith that are automatically operated by the controller 40, which flow control mechanisms may include valves and air detectors/pressure sensors. By having the valves and the detectors/sensors integral with the cassette 18, the lengths of the tubings interconnecting the various containers of the system 10 to the cassette 18 can be minimized, thus reducing the internal volume of the kit 14.

Specifically, the cassette 18 includes a first fluid pathway 54 with a first inlet 56 configured to be in fluid communication with container 20 of the suspension of cellular material to be washed. The first fluid pathway 54 further includes a second inlet 58 is in fluid communication with the container of wash media 22, and an outlet 60 in fluid communication with the inlet 42 of the spinning membrane separator 16.

The cassette 18 includes a second fluid pathway 62 having an inlet 64 in fluid communication with the first outlet 44 of the spinning membrane separator 16 to receive the retentate. The second fluid pathway further includes a first outlet 66 in fluid communication with the container 24 for receiving the retentate, and a second outlet 68 in fluid communication with the first syringe 28.

A third fluid pathway 70 is provided that includes an inlet 72 in fluid communication with the second outlet 46 of the spinning membrane separator 16 for flowing filtrate. The third fluid pathway 70 further includes a first outlet 74 in fluid communication with the container 26 for receiving the filtrate, and a second outlet 76 in fluid communication with the second syringe 30.

Devices for selectively occluding the fluid pathways are associated with each of the first, second and third fluid pathways 54, 62, 70. Such occluding devices may take the form of valves or clamps, and according to one embodiment may take the form of pinch valves. For ease of explanation, the devices for electively occluding the fluid pathways, irrespective of their structure, will be referred to as valves. As such, a first such valve 78 is associated with the 56 first inlet of the first fluid pathway 54, a second valve 80 is associated with the second inlet 58 of the first fluid pathway 54, a third valve 82 is associated with the inlet 64 of the second fluid pathway 62, a fourth valve 84 is associated with the first outlet 66 of the second fluid flow pathway 62, a fifth valve 86 is associated with the inlet 72 of the third fluid pathway 70, and a sixth valve 88 is associated with the first outlet 74 of the third fluid pathway 70.

Each of the first, second and third fluid pathways 54, 62, 70 is also provided with a sensor 90, 92, 94, respectively, that is able to detect differences in the fluid passing through the fluid pathways 54, 62, 70. Specifically, the sensors 90, 92, 94 are able to detect interfaces between different types of fluids, such as an air-liquid interface, a wash media-retentate interface, and a wash media-filtrate interface. Upon the detection of such interfaces, a signal is sent to the controller 40 that will act to control the configuration of the valves (open or closed) and actuate the syringe pumps 36, 38 to move fluid through the kit 14 in accordance with a cell washing procedure. The cassette 18 may also include a pressure sensor 96 for monitoring purposes.

Figure 5:
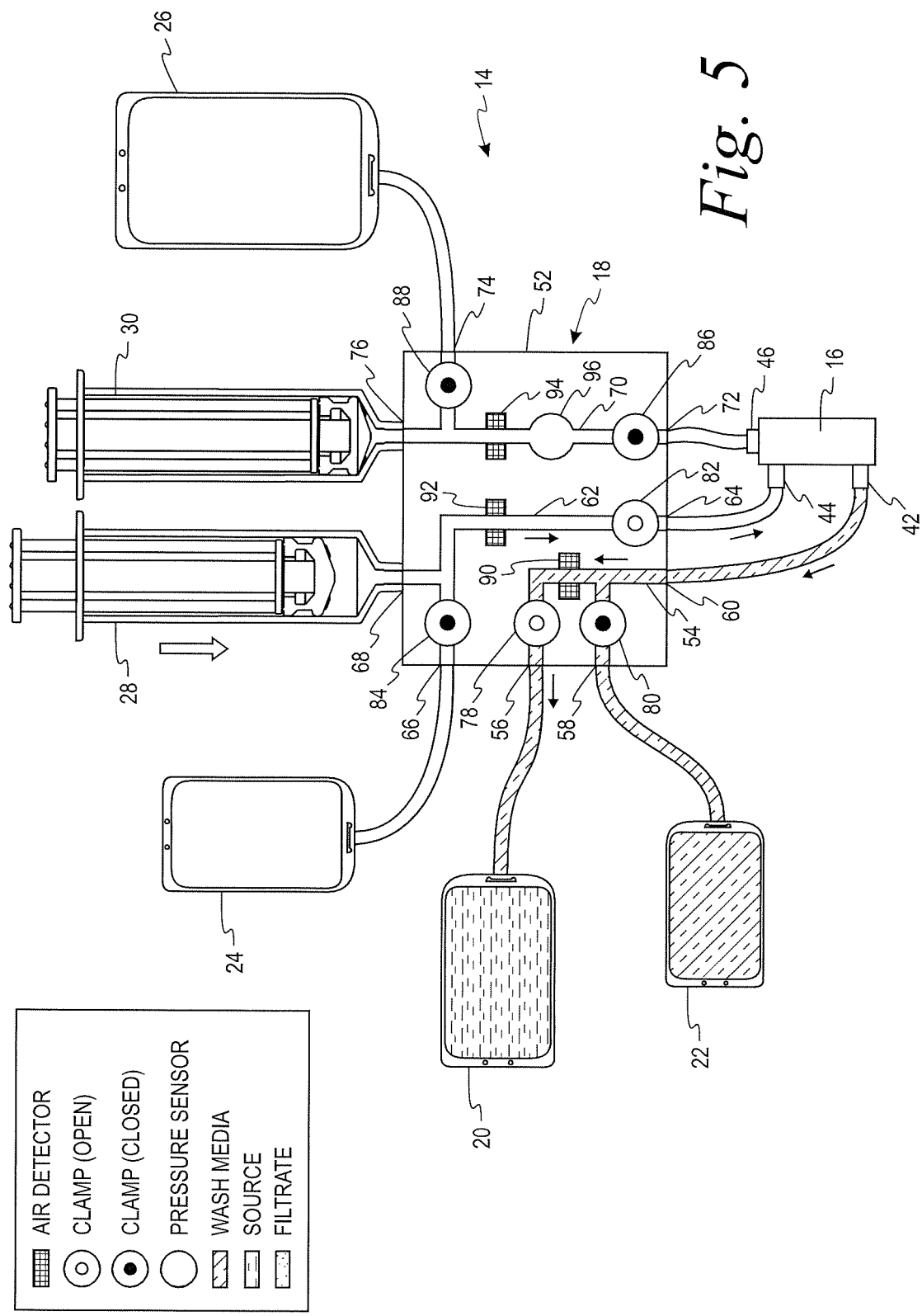
Figure 6:
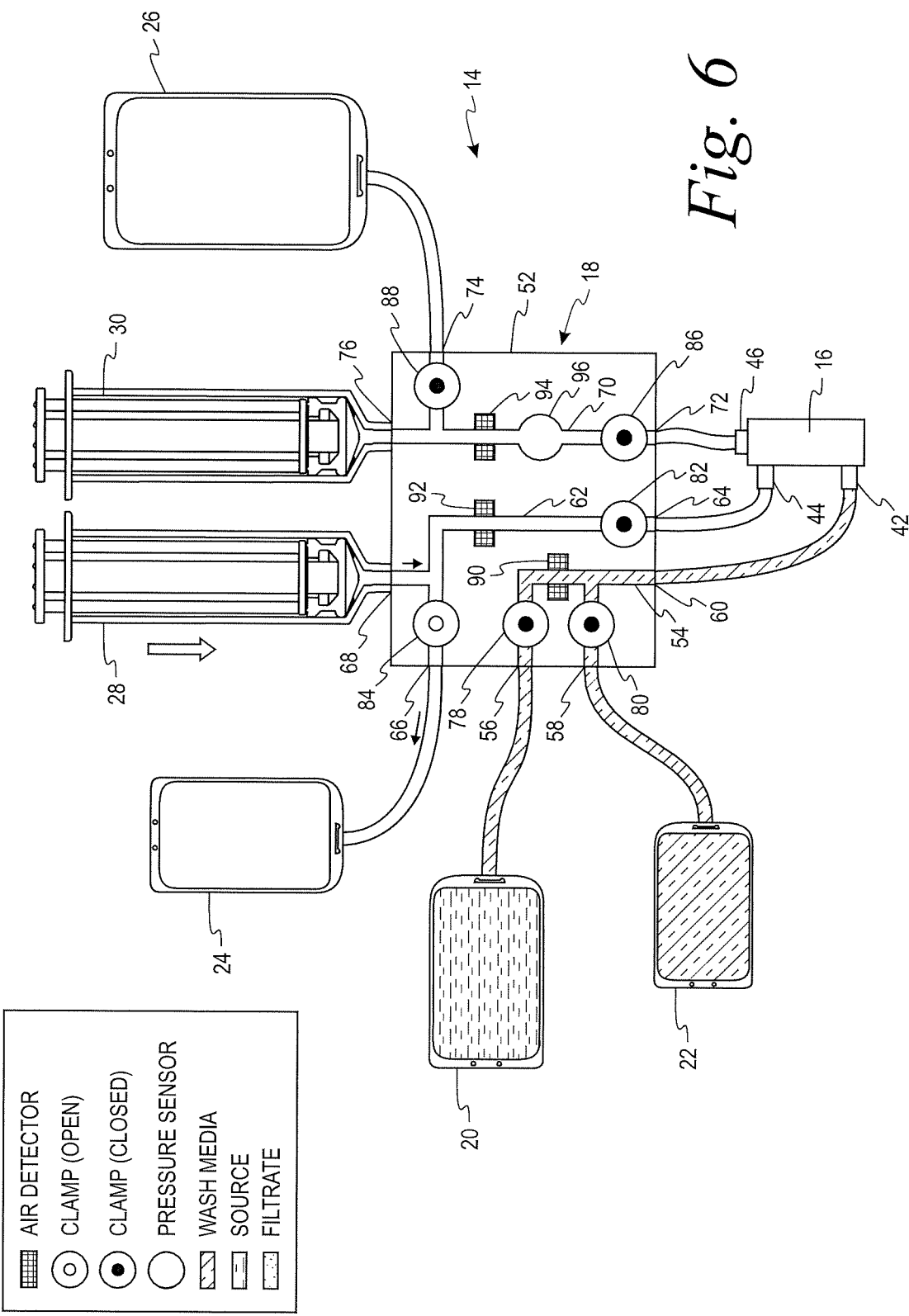
Figure 7:
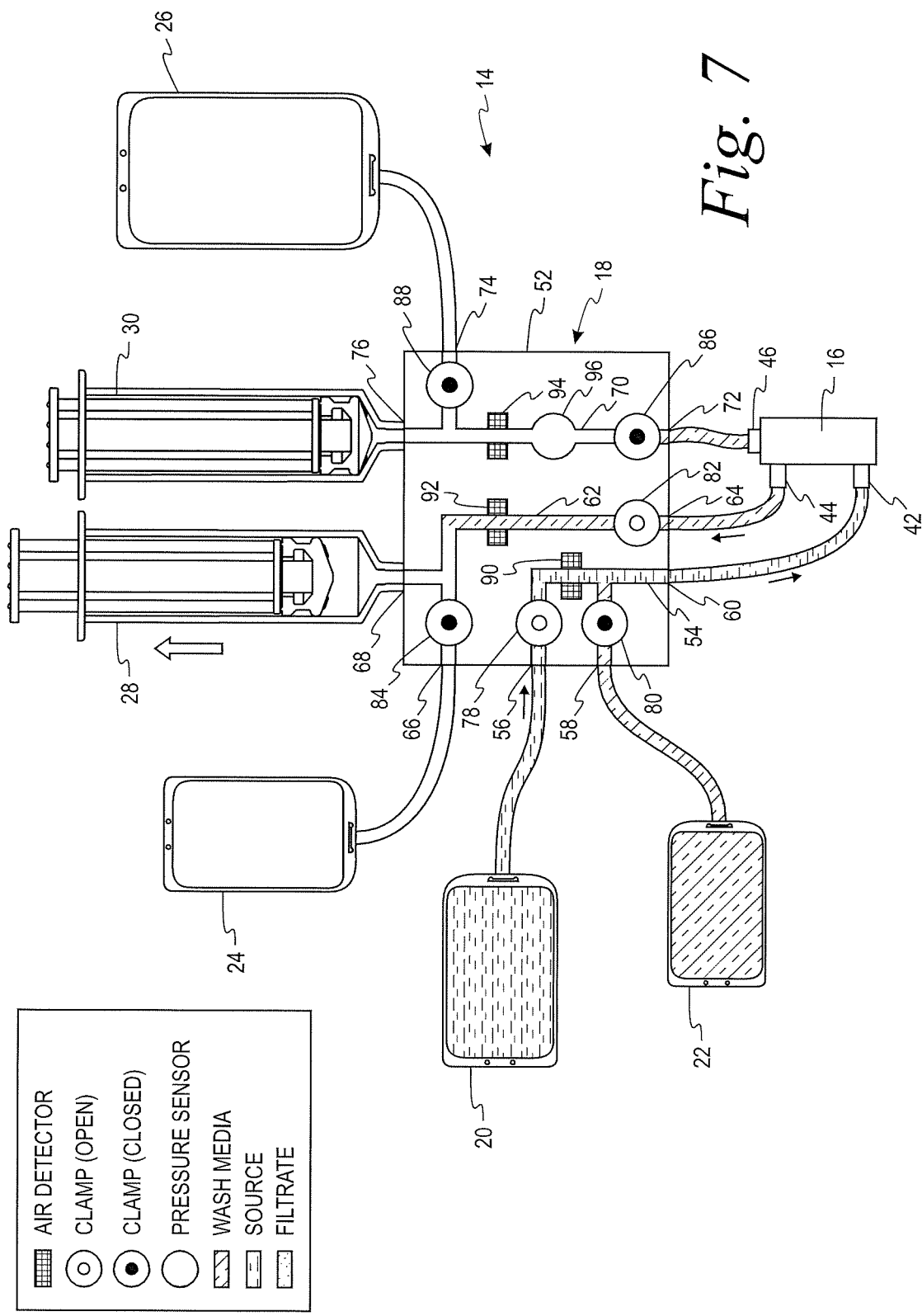
Figure 8:
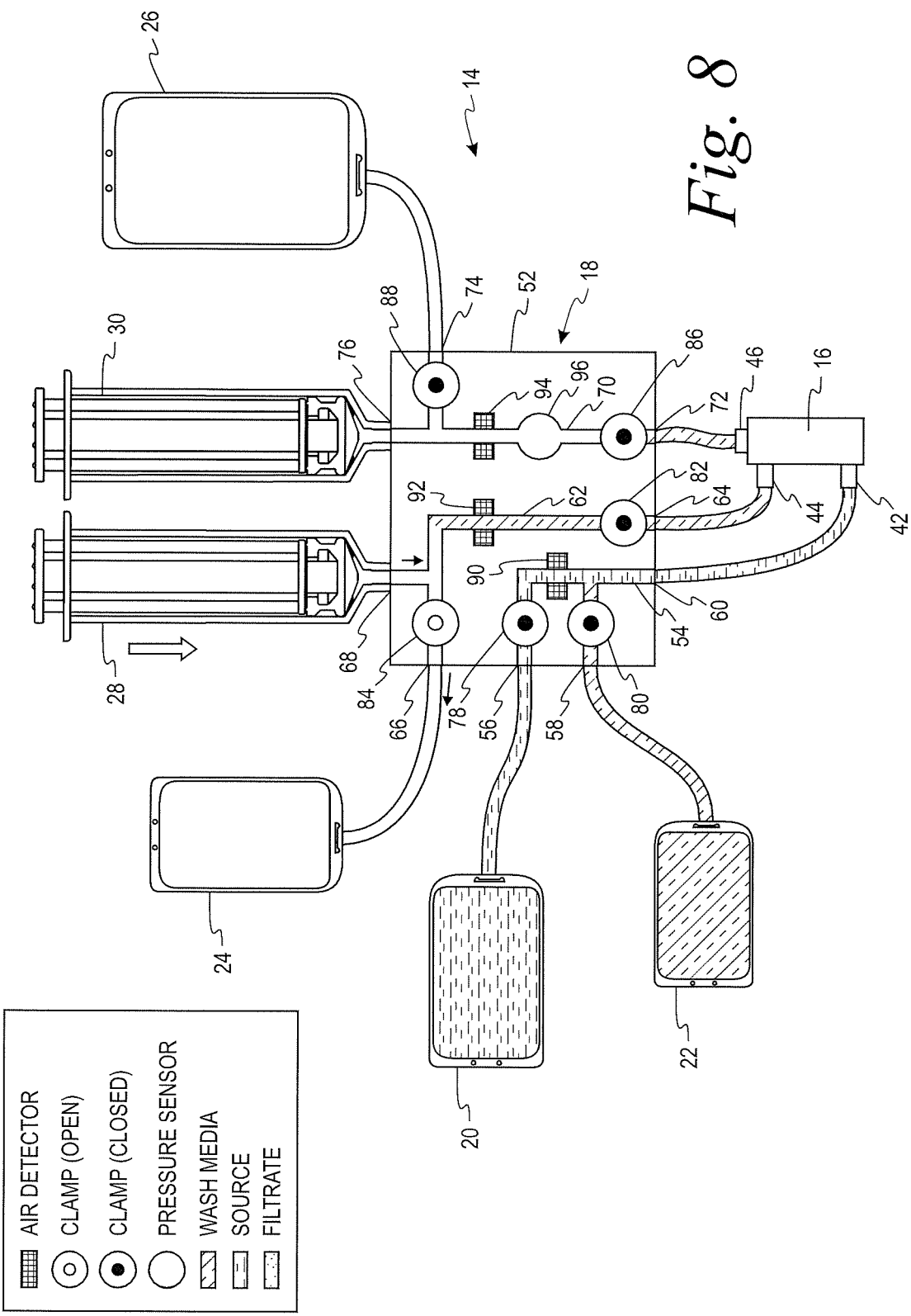
Figure 9:
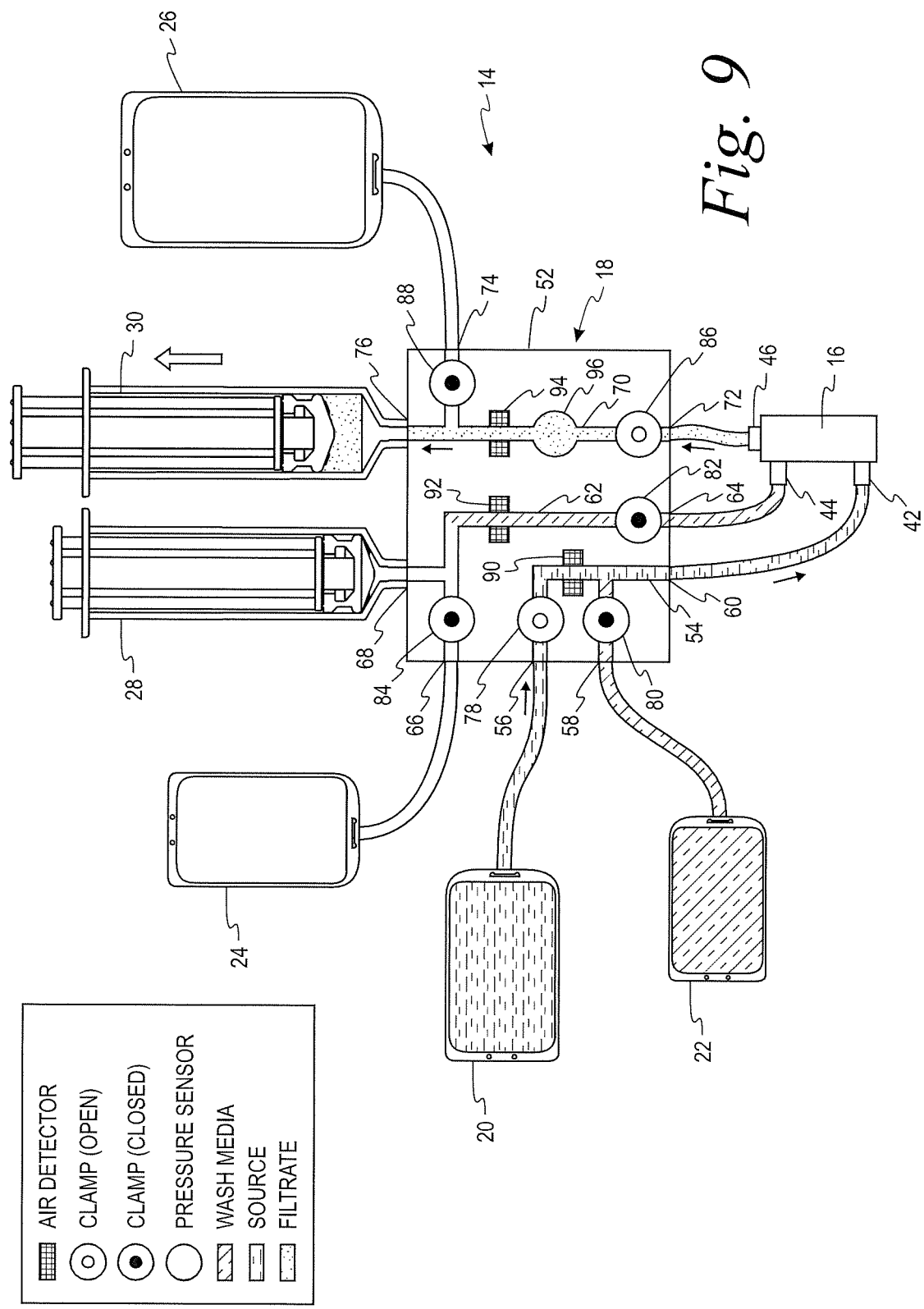
Figure 10:
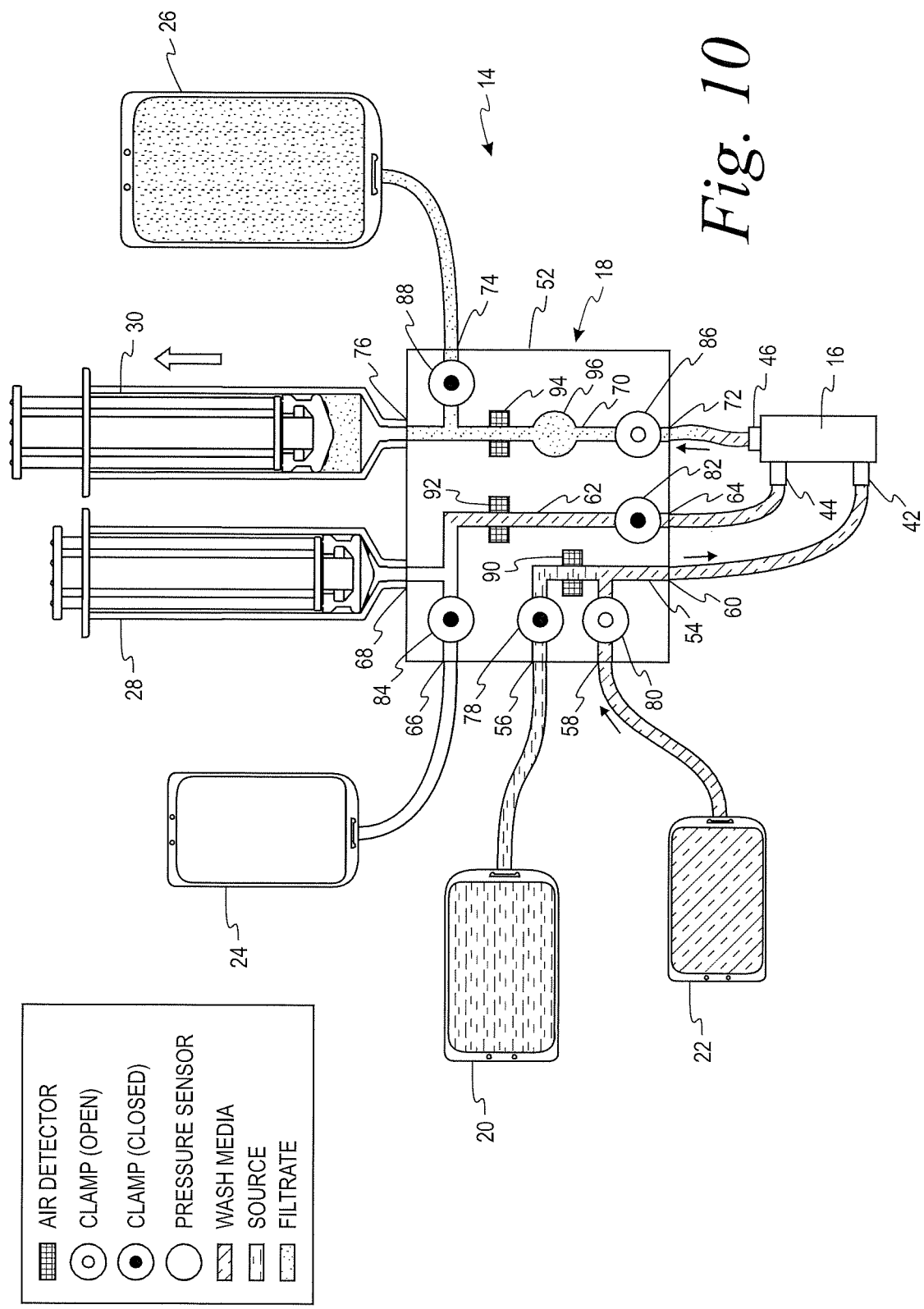
Figure 11:
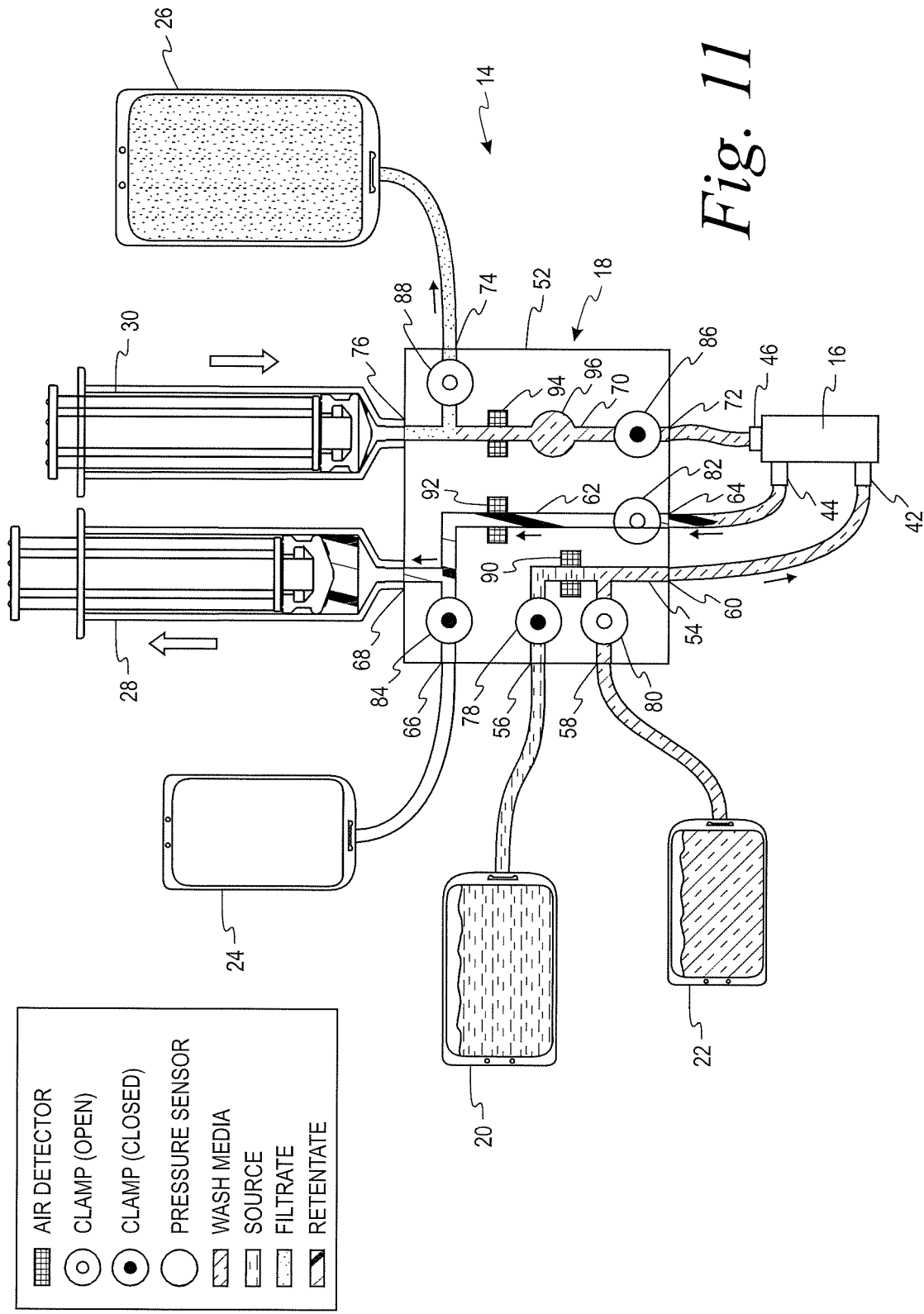

A cell washing procedure utilizing the system 10 set forth above will now be described. The procedure includes three relatively distinct phases: a priming phase, as illustrated in FIGS. 4-6, during which the kit 14 is primed with wash media; a loading phase, as illustrated in FIGS. 7 and 8, in which the annulus of the spinning membrane separator 16 is filled with the cellular suspension that is to be washed; and a wash phase, as illustrated in FIGS. 9-11, in which retentate (the washed cells) and filtrate (supernatant and wash media) are drawn through the cassette 18 and flowed to their respective containers 24, 26.

Once the disposable kit 14 is loaded onto the hardware component 12, with a container 20 of the cell suspension to be washed connected to the cassette 18, the cell washing procedure may commence. As is appreciated, the procedure may be automatically controlled by the programmable controller 40, which sequentially operates the valves 78, 80, 82, 84, 86, 88 and the syringe pumps 36, 38, in accordance with signals received from the sensors 90, 92, 94, 96.

The priming sequence, as illustrated, may include three steps, or it may include one or more of the following three steps, or one or more subparts of these steps.

Figure 4:
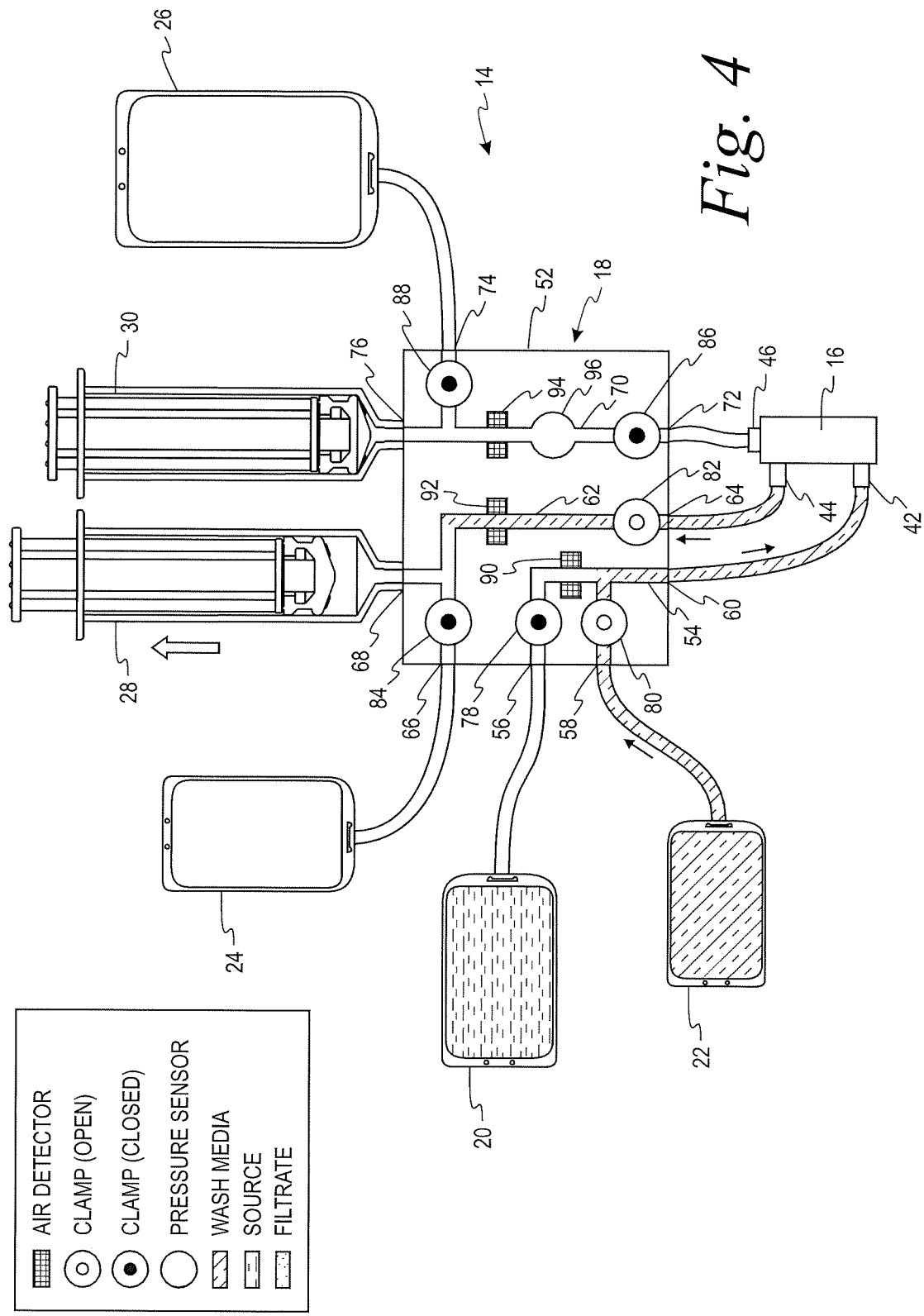
FIGS. 4-15 are schematic views of the disposable kit of FIG. 2 showing the configuration of the kit during the various stages or phases of a cell washing procedure, with FIGS. 4-6 illustrating the priming phase of the procedure, FIGS. 7-11 illustrating the steps of the first wash phase, and FIGS. 12-15 illustrating the steps of a subsequent wash phase.

In a first step, shown in FIG. 4, the first fluid flow path 54 is primed with wash media from the second inlet 58 to the valve 78 adjacent the first inlet 56 for the source container 20 and to the outlet 60 connecting with the inlet 42 of the separator 16. In this step, the plunger of the first syringe 28 is withdrawn with valves 78, 84, 86 closed and valves 80, 82 open, thus drawing wash media out of the container 22 into the first fluid pathway 54. Wash media is drawn through the spinning membrane separator 16 and out the first outlet 44 into the second fluid pathway 62 until the sensor 92 detects an air-fluid interface, at which time the syringe pump 36 is stopped and the plunger of the first syringe 28 no longer withdrawn. Alternatively, withdrawal (and depression) of the plunger can be controlled based on changes in volume within the barrel of the syringe that is correlated to volumes of fluid drawn through the kit. The disposable kit 14 may instead be primed with wash media by drawing wash media from its source 22 only up to the inlet 58 to the first fluid pathway 54, to further reduce the volume of wash media.

In a second step of the priming sequence, shown in FIG. 5, the plunger of the first syringe 28 is at least partially depressed, with valve 78 open and valve 80 closed, to prime the first fluid pathway 54 to the source container 20, thus completing the priming of the first fluid pathway.

In a third step of the priming sequence, shown in FIG. 6, the plunger of the first syringe 28 is completely depressed, so that no air remains in the syringe, with valves 78 and 82 closed and valve 84 open, to vent air to the retentate container 24 (or, alternatively, the sterile vent 50 which is removably attached to the kit 14 for this purpose, and may be attached at other times when air is being vented from the kit or circuit 14). While not shown in the drawings, the third fluid flow path 70 may also be primed with wash media by withdrawing the plunger of the second syringe 30 with valves 78, 82, 88 closed and valves 80, 86 open, to draw wash media into the third fluid pathway 70. The air drawn into the second syringe 30 would then be vented into the filtrate container 26 (or the sterile vent 48 removably attached for this purpose, similar to the sterile vent 50 mentioned above) by closing valve 86 and opening valve 88 and completely depressing the plunger.

The system 10 is now ready for loading the annulus of the spinning membrane separator 16 with the suspension of cells to be washed. With reference to FIG. 7, this is accomplished by withdrawing the plunger of the first syringe 28 with valves 78, 82 open and valve 84 closed. This draws cell suspension out of the source container 20 into the first fluid pathway 54 and through the spinning membrane separator 16. The wash media in the first fluid pathway 54 that resulted from priming is drawn into the second fluid pathway 62. The withdrawal of the plunger of the first syringe 28 is stopped when the annulus of the separator 16 is filled with cell suspension, and prior to the cell suspension reaching the second fluid pathway 62, as determined by, e.g., detection of an air-fluid interface by sensor 92, or upon a change in volume of the barrel of the syringe 28. The air drawn into the syringe 28 due to loading the separator 16 is then vented to the retentate container 24 (or to the sterile vent 50, as will be recognized with reference to the discussion above) by completely depressing the plunger of the first syringe 28 with the valve 82 closed and the valve 84 open, as shown in FIG. 8.

The supernatant is then separated from the cell suspension by the separator 16 (as operated in conjunction with the drive 32) and removed. With reference to FIG. 9, this is accomplished by withdrawing the plunger of the second syringe 30 with valves 78, 86 open and valves 80, 82, 88 closed. As such, additional cell suspension is drawn into the separator 16 as the supernatant flows out of the separator 16 through outlet 46, into the third fluid flow path 70 and into the barrel of the second syringe 30, while cellular content accumulates in the annulus of the separator 16.

Withdrawal of the plunger of the second syringe 30 continues drawing supernatant into the barrel until the cellular content of the annulus of the separator 16 is exceeds the configured volume (based on an empirical determination of the internal volume of the spinner annulus, the rotational velocity of the spinner, the filtrate flow rate). Alternatively, the plunger of the second syringe 30 continues to draw supernatant into the barrel of the second syringe 30 until it is filled with supernatant, or the sensor 90 detects an air fluid interface, indicating that the source container 20 is empty.

The cells accumulated in the annulus of the separator 16 are then washed. With reference to FIG. 10, this is accomplished by further withdrawing the plunger of the second syringe 30 with valve 78 closed and valve 80 open, valves 82, 84, 88 remaining closed. As such, wash media is drawn into and through the separator 16 into the second syringe 30. The plunger of the syringe 30 continues to be withdrawn until it is either filled or container 22 is emptied of wash media.

The cells accumulated in the annulus of the separator 16 are then withdrawn to clear the annulus. As illustrated in FIG. 11, the plunger of the first syringe 28 is withdrawn with valve 82 opened and valve 78, 84, 86 closed, thus drawing the washed cells into the barrel of the first syringe 28. In addition, if the source container 20 contains additional cell suspension that is to be washed, the second syringe 30 can be prepared by expelling the supernatant/wash media contained in the second syringe 30 into the filtrate container 26 by depressing the plunger of the second syringe 30 with the valve 86 closed and the valve 88 open, as is also illustrated in FIG. 11.

If additional cell suspension is contained in the source container 20, it can be washed by repeating the steps illustrated in FIGS. 9-11, as described above, until the container 20 is depleted. At the completion of each wash cycle, the washed cells contained in the first syringe 28 may be expelled into the retentate container 24 by fully depressing the plunger of the first syringe 28 with valve 84 open and valve 82 closed.

Alternatively, subsequent wash cycles may be performed as illustrated in FIGS. 12-15.

Figure 12:
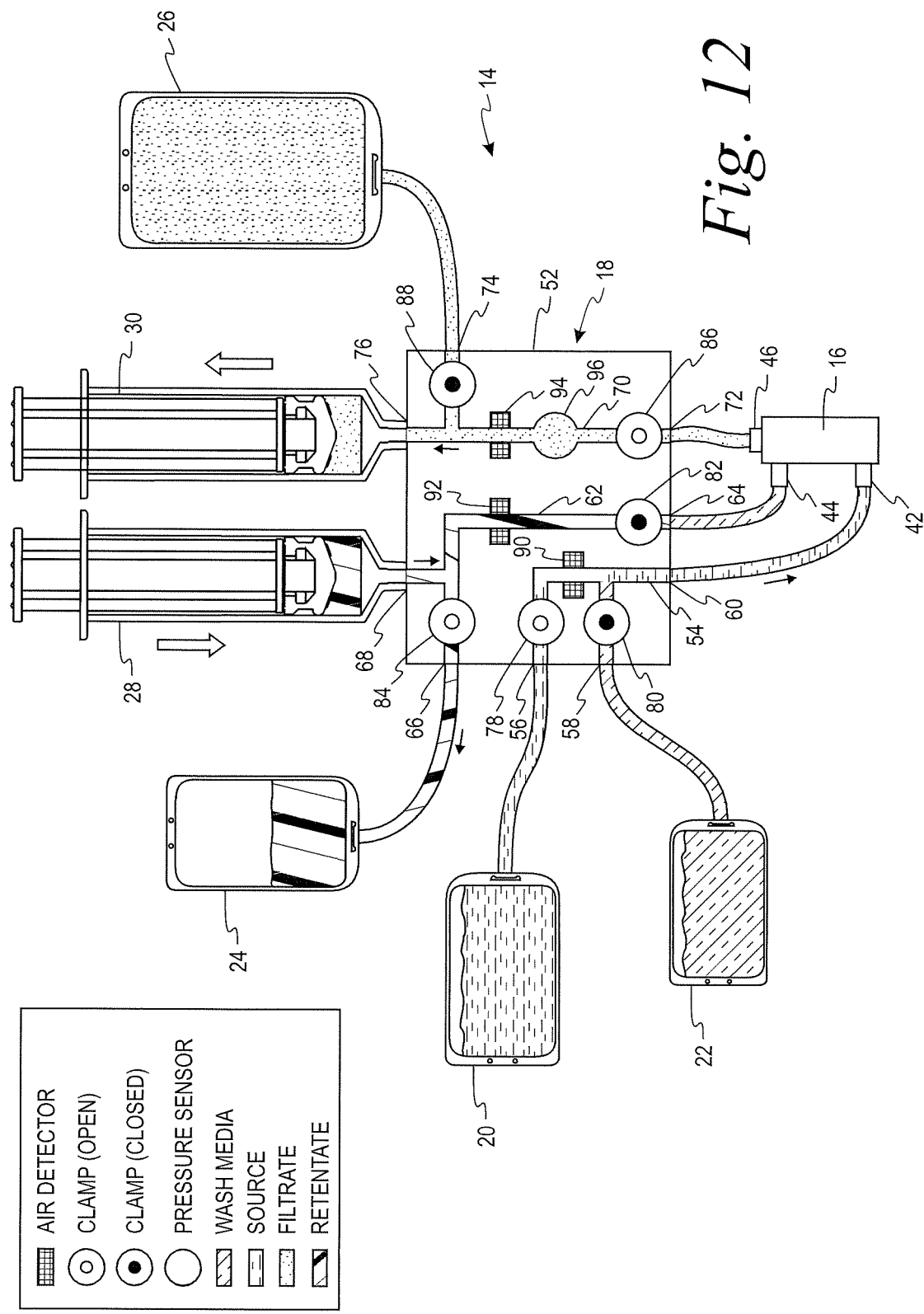
Figure 13:
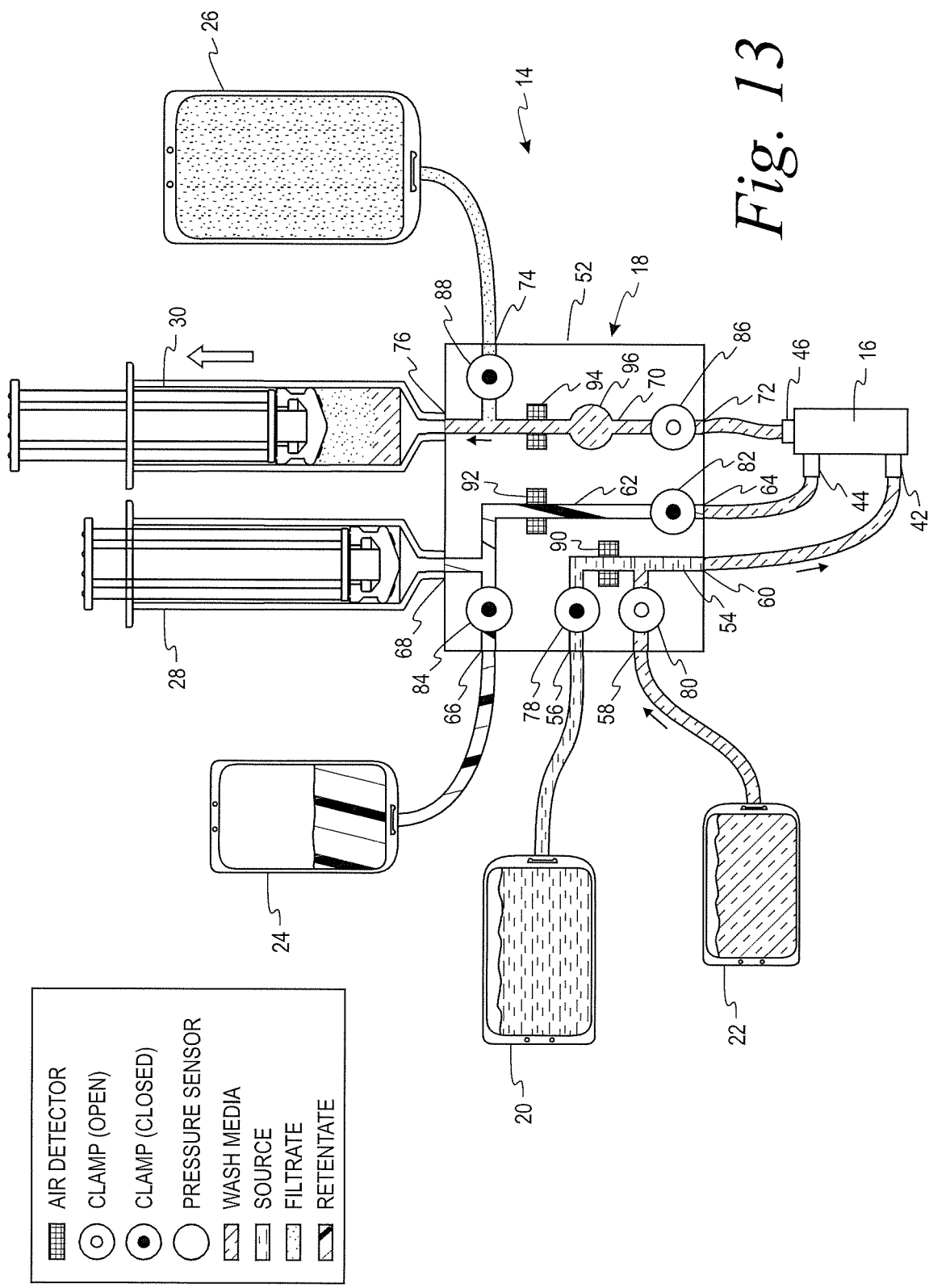
Figure 14:
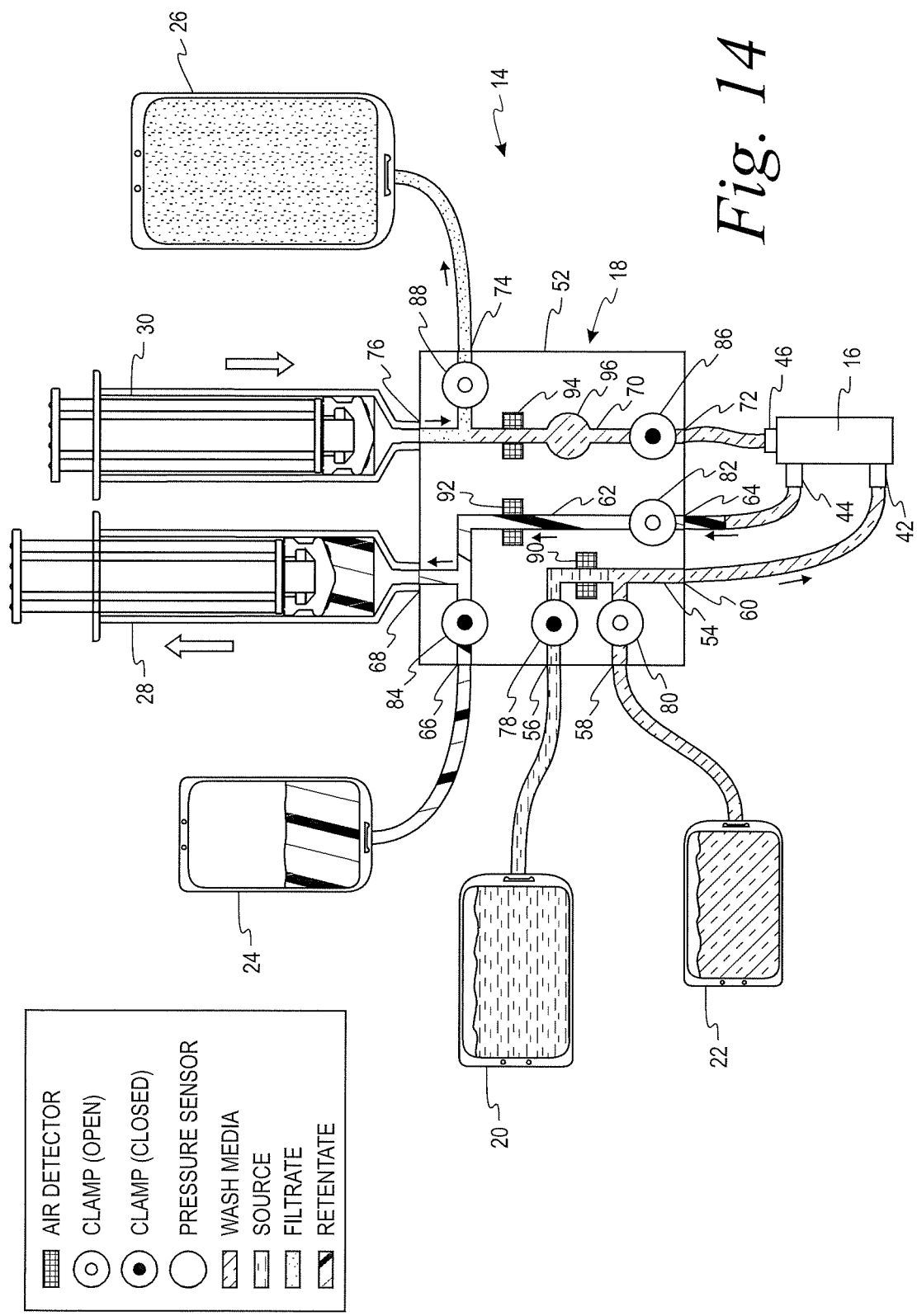
Figure 15:
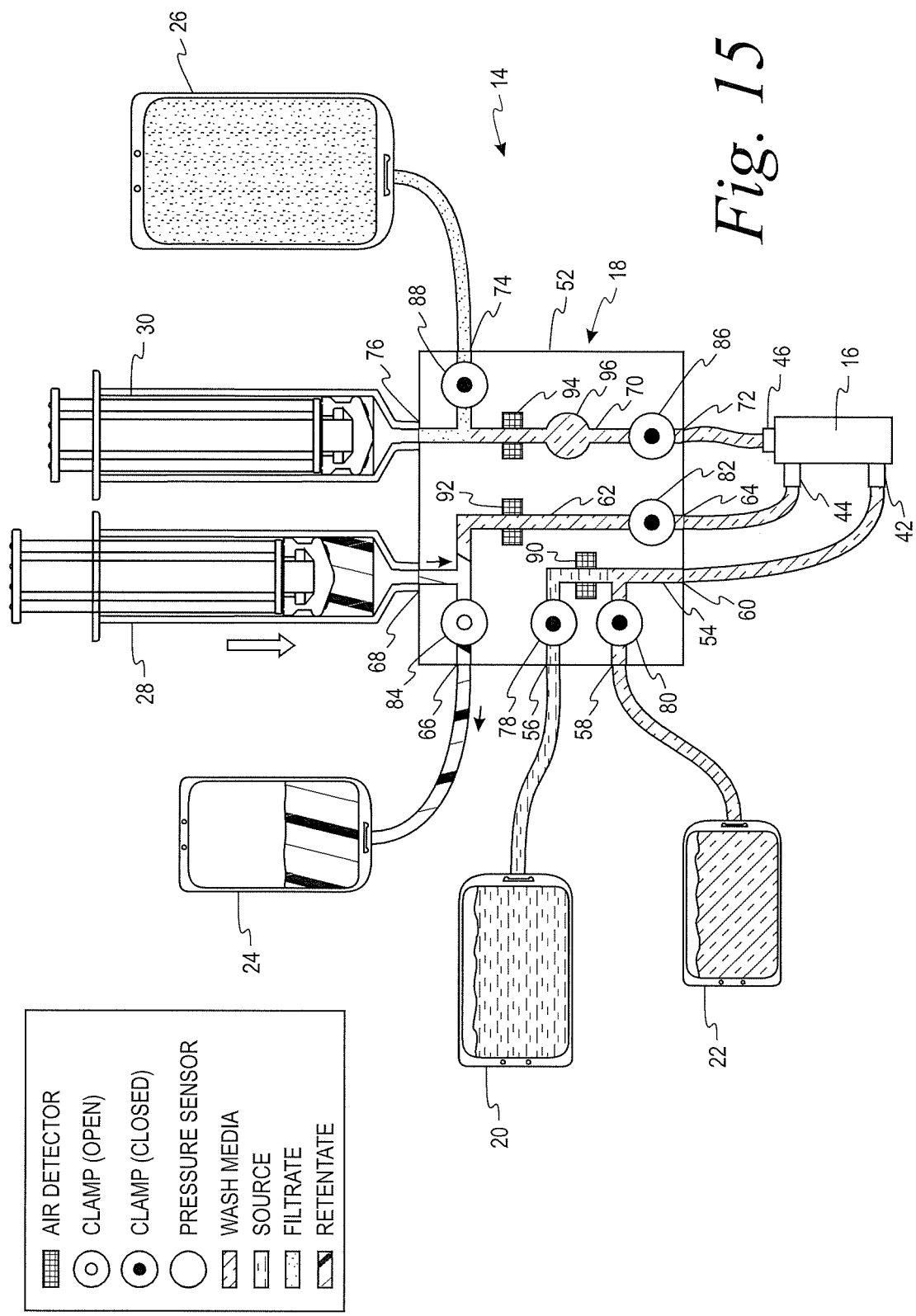

Specifically, a second or subsequent volume of cell suspension is pulled from the source container 20 into the annulus of the separator 16 by closing the valves 80, 82, 88, opening the valves 78, 86, and withdrawing the plunger of the second syringe 30 (FIG. 12). At the same time, the previous cycle's washed retentate is pushed into the retentate container 24 by opening the valve 84 and depressing the plunger of the first syringe 28. Next, the supernatant in the cell suspension is removed by closing the valve 78 and opening the valve 80, so that additional wash media is drawn from the container 22 into the annulus of the spinner 16 by further withdrawing the plunger of the second syringe 30 (FIG. 13). Further, the annulus of the spinner 16 is cleared by opening the valve 82 and withdrawing the plunger of the first syringe 28, thus drawing the retentate into the syringe 28 (FIG. 14). In addition, the filtrate in the second syringe 30 may be pushed into the filtrate container 28 with the valve 86 closed, the valve 88 open, and depressing the plunger of the second syringe 30. The retentate in the first syringe 28 is then pushed into the retentate container 24 by closing the valves 80, 82, opening the valve 84, and depressing the plunger of the first syringe 28 (FIG. 15).

The steps illustrated in FIGS. 12-15 may be repeated until the source container 20 is emptied of cell suspension.

Figure 16:
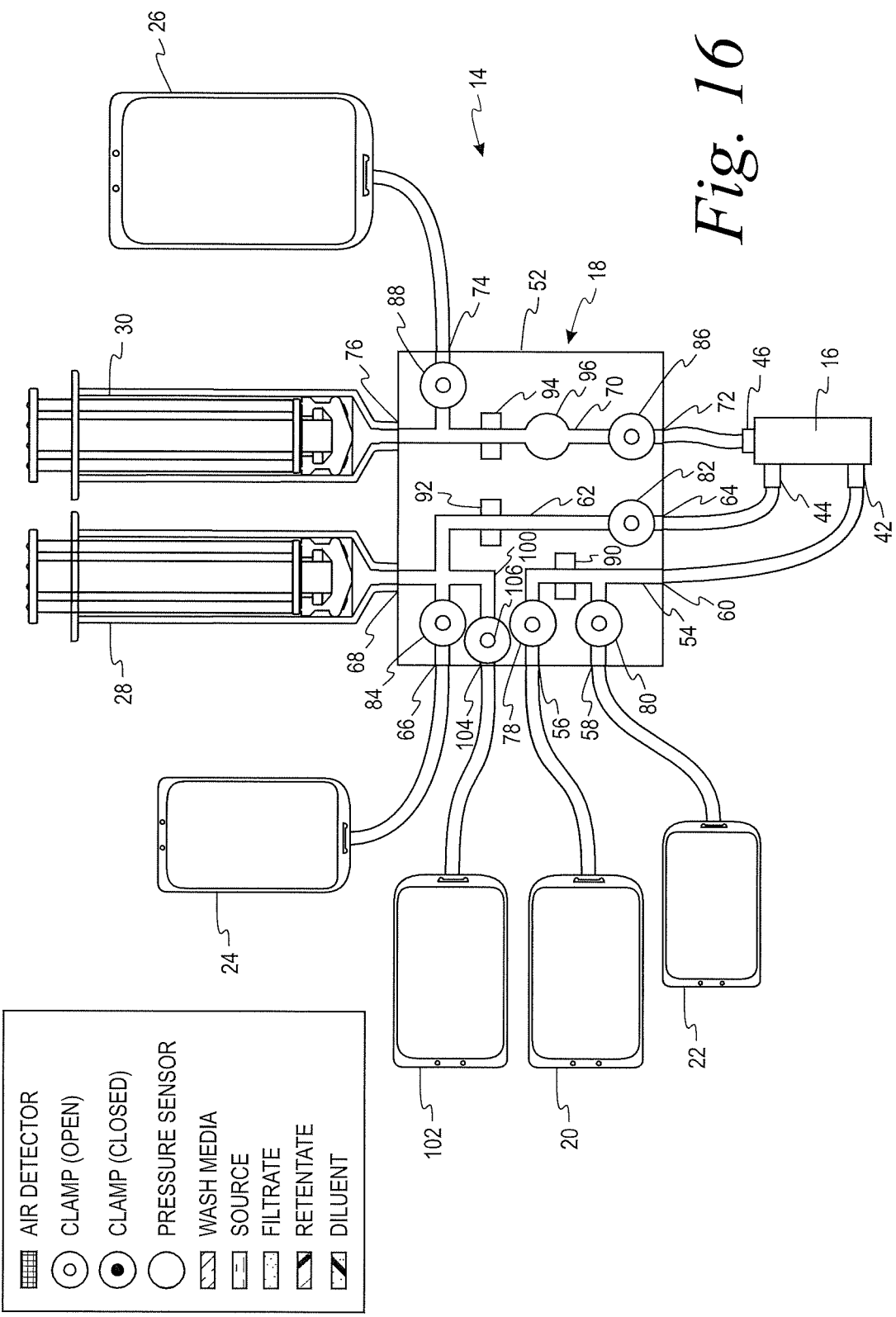
FIG. 16 is a schematic view of a second embodiment of a disposable kit for use in the system of FIG. 1 that permits the addition of a diluent to the washed cells.

Under certain circumstances, it may be desirable to dilute the washed cells comprising the retentate, for example if the retentate is to be frozen, in which case a cryoprotective agent would be used to dilute the retentate. To this end, and as illustrated in FIG. 16, the cassette 18 may be provided with a further, fourth fluid pathway 100 that provides fluid communication between the first syringe 28 and a container 102 for the diluent. The fluid pathway 100 includes an inlet 104 and a valve 106 adjacent the inlet 104 for controlling fluid flow through the pathway 100.

Figure 17:
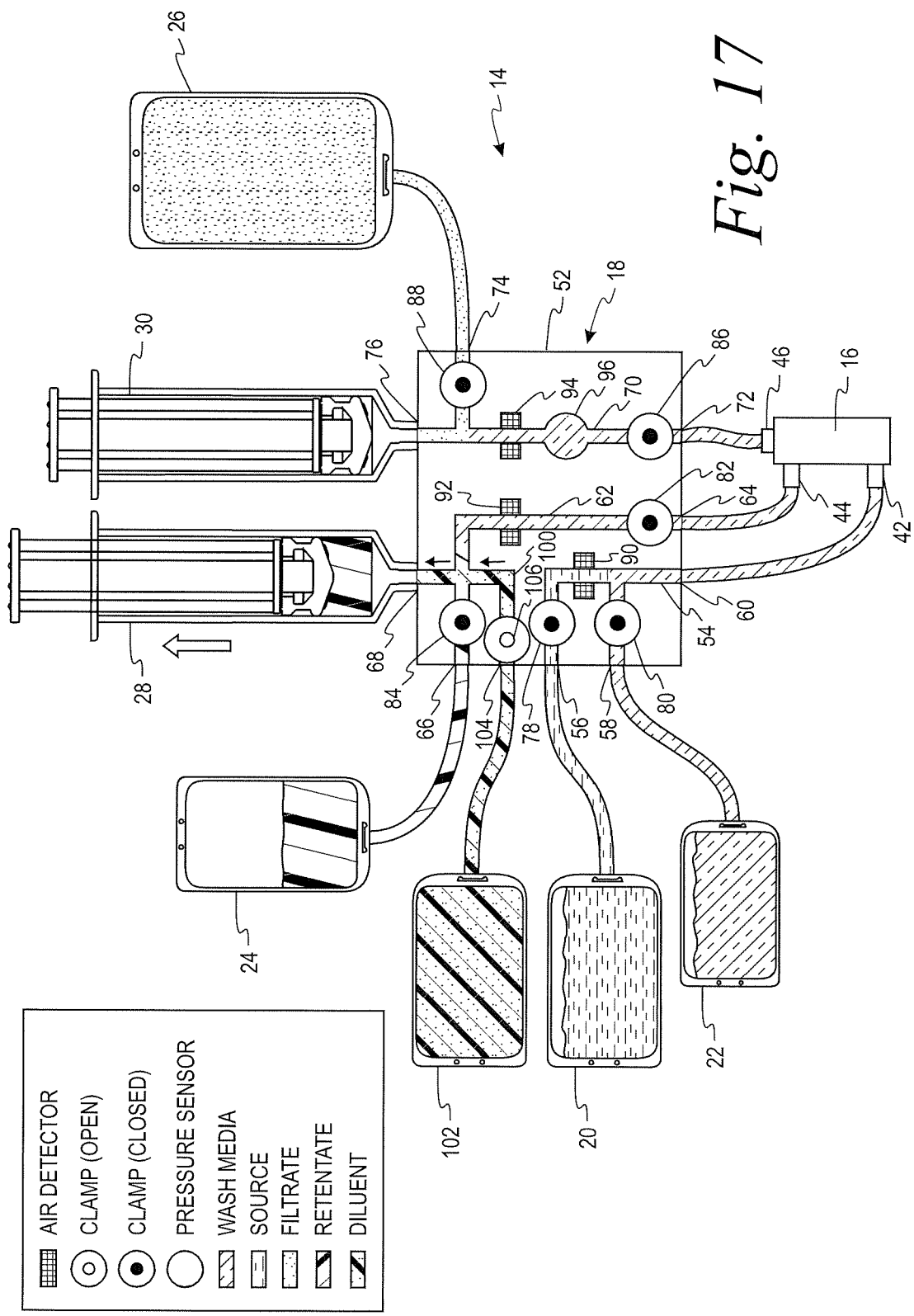
FIGS. 17 and 18 are schematic views of the disposable kit of FIG. 16 illustrating the steps of adding a diluent to the washed cells
Figure 18:
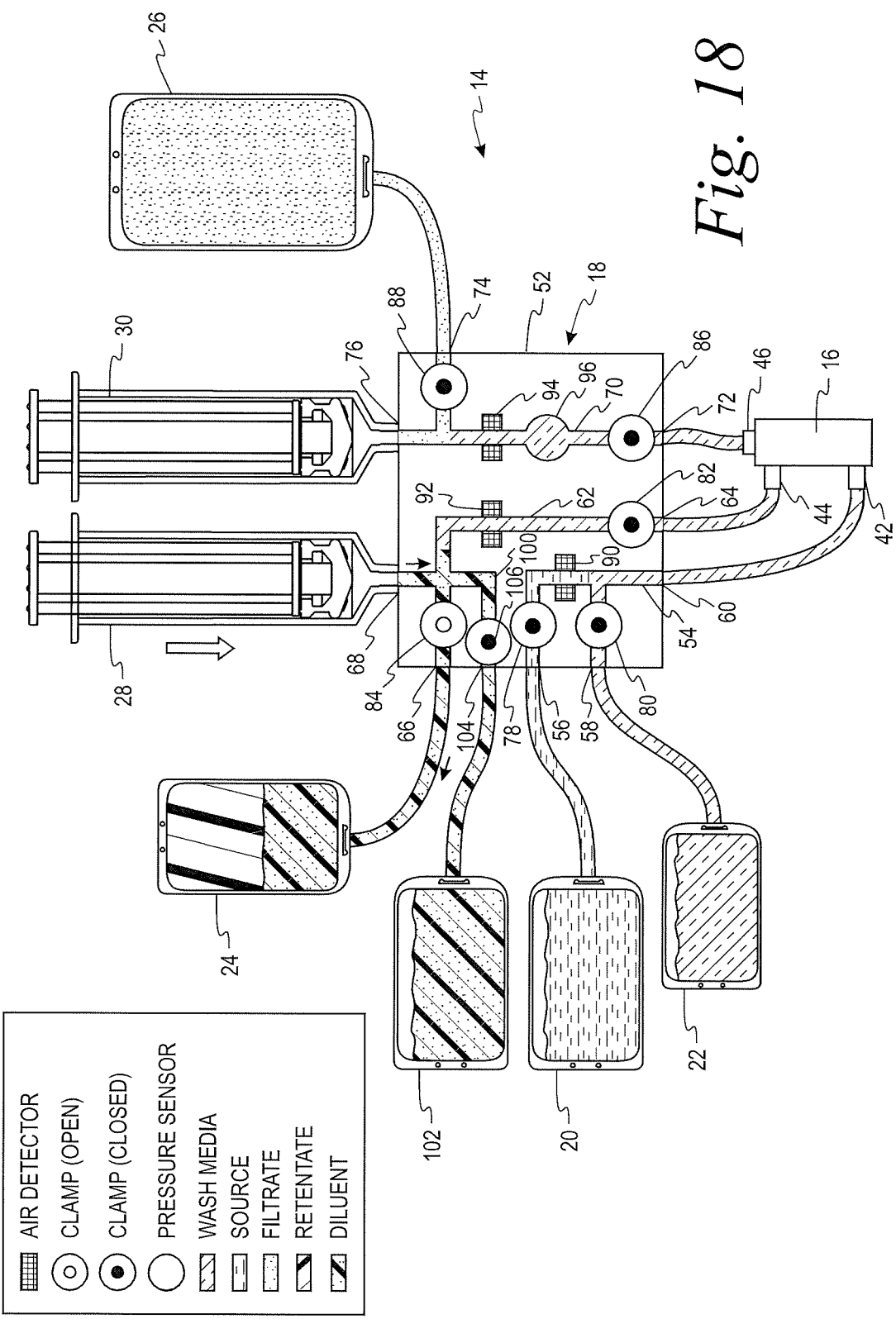

To add a diluent to the retentate in the container 24, the valves 82 and 84 are closed, while the valve 106 is opened. The plunger of the first syringe 28 is withdrawn to flow diluent out of the container 102 and into the syringe 28 (FIG. 17). Then, the valve 106 is closed and the valve 84 opened. The plunger of the first syringe 28 is then depressed to push diluent into container 24 (FIG. 18).

As mentioned above, an advantage of the system 10 is that it can be used to process small volumes, certainly much smaller volumes than are possible using conventional equipment. Further, because such small volumes are being processed, it becomes desirable to provide a mechanism for filling the cell product processed using the system 10 directly into low-volume containers (e.g., between 1 mL and 50 mL), such as may be used to administer the cell product. For example, such a low-volume container may be a syringe, which low-volume container may also serve as a delivery container (e.g., for administration to a patient), and may be a single-use (delivery) container (e.g., for administration to a patient with disposal of the container thereafter).

Figure 19:
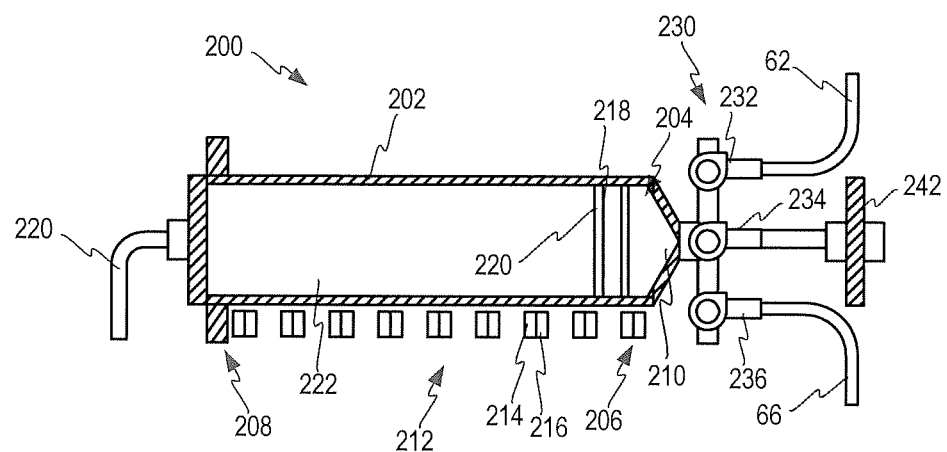
FIG. 19 is a cross-sectional view of an embodiment of a syringe/syringe pump as may be used as part of the system of FIGS. 1 and 2, with a plunger head assembly in a first position.
Figure 20:
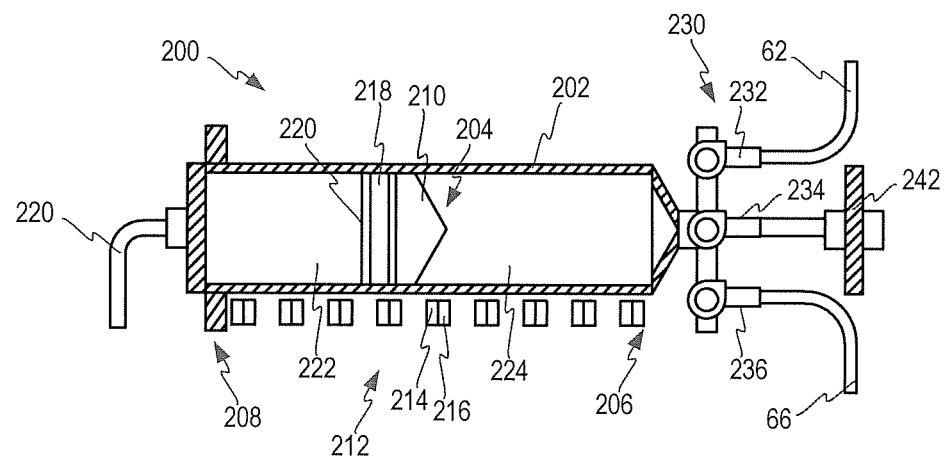
FIG. 20 is a cross-sectional view of the syringe/syringe pump of FIG. 19, with a plunger head assembly in a second position.

When filling such low-volume containers, it is important to provide controlled delivery of the cell product to the low-volume container. FIGS. 19 and 20 illustrate an embodiment of a syringe/syringe pump 200 that may be used to fill low-volume containers, which syringe/syringe pump 200 may be substituted for the syringe 28 and syringe pump 36, for example, or may be used in conjunction with the system 10 in place of the container 24. FIGS. 22-28 illustrated another embodiment of a syringe/syringe pump 300 that may be used to fill low-volume containers, specifically the syringe component of the syringe/syringe pump 300. This syringe/syringe pump 300 may be used in place of the syringe 28 and syringe pump 36, or may be used in conjunction with the system 10 in place of the container 24. For ease of explanation, the combination of syringe and syringe pump 200, 300 shall be referred to simply as syringe pump 200, 300 herein.

It will be recognized that aspects of the syringe pumps 200, 300 may be advantageously incorporated into the system 10, even if the syringe pumps 200, 300 are not used for filling low-volume containers (e.g., syringes). For example, the filtered pneumatic system used to move the piston or plunger head back and forth along the length of the barrel may be used with the remainder of the system 10 as described above, even if the syringe pump is not used to fill low-volume containers.

Turning first to the embodiment of the syringe pump 200 illustrated in FIGS. 19 and 20, the syringe pump 200 includes a syringe barrel 202 (which may be made of cyclic olefin copolymer, or other materials such as may be inert, optically clear and, for certain applications, liquid-nitrogen compatible) and a piston or plunger head assembly 204. The plunger head assembly 204 is moveable (translatable) between a first end 206 and a second end 208 of the barrel 202.

The plunger head assembly 204 includes the plunger 210 and one part of a position detector 212. According to the illustrated embodiment, the position detector 212 also includes a plurality of transmitter/sensor pairs 214, 216. According to the illustrated embodiment, the transmitters (or emitters) 214 may be in the form of infrared light emitting diodes, and the sensors 216 may be in the form of infrared sensors. According to other embodiments, the transmitters and sensors may use visible or ultraviolet light, for example. The transmitter/sensor pairs 214, 216 are disposed along the length of the barrel 202 between the first end 206 and the second end 208. The pairs 214, 216 operate in conjunction with an infrared reflector 218 that is part of the plunger head assembly 204. As one example, the reflector 218 may be in the form of a reflective strip that is disposed about the perimeter of a rigid disc 220 that is attached opposite the plunger 210.

Figure 21:
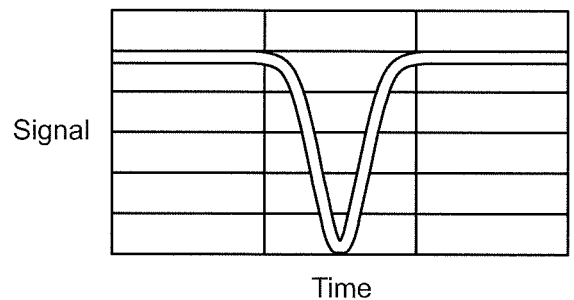
FIG. 21 is a chart of the signal response of one of the infrared detectors or sensors of the syringe/syringe pump of FIG. 20.

In operation, the position detector 212 (which could be coupled to the controller 40, for example) would use the interaction between the transmitter/sensor pairs 214, 216 and the reflector 218 to determine the position of the plunger head assembly 204 along the barrel 202. In particular, light emitted from the transmitter 214 would be received by the sensor 216 (or would be received over a threshold amount) if the light contacts the reflector 218. Otherwise, the light would not be received by the sensor 216 (or would not be received below the threshold amount). Depending on the amount of light received by the sensor 216, a signal generated by the sensor 216 would vary (see, e.g., FIG. 21). Depending on the signals received from the individual transmitter/sensor pairs 214, 216, the controller 40 may determine the position of the plunger head assembly 204 along the barrel 202 between the first and second ends 206, 208.

A vacuum/pressure source (e.g., a diaphragm pump) is attached via line (e.g., tubing) 220 to the end 208 of the barrel 202. The end 208 is otherwise closed, forming a first variable volume space 222 between the closed end 208 of the barrel 202 and the plunger head assembly 204. Filtered air may be pumped into and out of the space 222 to cause the plunger head assembly 204 to move between the first and second ends 206, 208 of the barrel 202. According to embodiments where the syringe pump 200 is used in conjunction with the system 10, the vacuum/pressure source instead may permit the plunger head assembly 204 to move in response to the action of the syringe 28/syringe pump 36 pushing fluid into the barrel 202, by venting the space 222, for example. The movement of the plunger head assembly 204 causes a second variable volume space 224 to open between the plunger head assembly 204 and the first end 206 to receive fluid (e.g., a cell product) into the barrel 202. Compare FIGS. 19 and 20. Fluid may be drawn into (or may enter into) and ejected or delivered from the space 224 according to the movement of the plunger head assembly 204.

A set 230 of as many as three valves 232, 234, 236 is attached to the end 206 of the barrel 202. The set of valves 230 may be coupled to the controller 40 (potentially via other equipment, such as motors); the set 230 may be coupled as a group, or as individual valves 232, 234, 236. According to one use of the syringe pump 200, the syringe pump 200 may take the place of the syringe 28 and syringe pump 36 of the system 10 as explained above. As such, the valves 232, 236 may correspond to the valves 82, 84, and valves 232, 236 may connect the barrel 202 to the spinning membrane 16 via the fluid pathway 62, and to a low-volume container via the outlet 66. While the valves 232, 236 may appear as stopcocks in the illustration of FIG. 19, the structures (e.g., pinch valves) defining valves 82, 84 discussed above may be used in the place of the illustrated stopcocks. The valve 234 connects the barrel 202 to a filtered vent 242 to permit the barrel 202 to vent to atmosphere, for example, and it too may be incorporated into the embodiment of the system 10 as illustrated in FIGS. 1 and 2.

In operation, the plunger head assembly 204 starts at a first position, such as is illustrated in FIG. 19. The controller 40 opens the valve 232 and causes the vacuum/pressure source to operate, and draw vacuum behind the plunger head assembly 204 (i.e., space 222). As a consequence, the plunger head assembly 204 moves in the direction of the end 208 (i.e., from the end 206 to the end 208) and draws fluid from the annulus of the spinning membrane 16 via the second fluid pathway 62 into the space 224 (see FIG. 20). The controller 40 may subsequently close valve 232, open valve 236 and operate the vacuum/pressure source to pump pressurized air into the space 222. This causes the plunger head assembly 204 to move in the direction of the end 206 (i.e., from the end 208 to the end 206) and push fluid to the low-volume container via the outlet 66 from the space 224. The low-volume container may be a syringe, for example, with the outlet 66 in fluid communication with the barrel of the syringe via a tip of the syringe, for example.

To limit the fluid remaining in the barrel 202, the controller 40 may close the valve 236, open the valve 234 and cause the vacuum/pressure source to operate to draw vacuum behind the plunger head assembly 204. As a consequence, air is drawn through the filtered vent 242 into the space 224. The controller 40 then closes the valve 234, opens the valve 236, and causes the vacuum pressure source to operate to pump pressurized air into the space 222. This causes the plunger head assembly 204 to again move in the direction of the end 206 and push any remaining fluid to the container (e.g., syringe) via the outlet 66. Any remaining air may be subsequently exhausted through the vent 242.

It will be recognized that the pneumatic control of filtered air in and out of the space 222 provides certain advantages over the use of a syringe with a plunger arm where one end of the barrel remains open to the surrounding environment. By leaving the barrel end open, materials could collect on an inner surface of the barrel wall, such that movement of the plunger head between the ends could permit the materials on the inner surface to interact with the fluid on the other (i.e., wet-side) of the plunger head. The use of filtered air in the space 222 to move the plunger 210 reduces or eliminates this potential source of contaminants. Further, the position detector 212 permits very precise control of the operation of the syringe pump 200. Because these advantages are not limited to the use of the syringe pump 200 (in whole or in part) in place of the syringe 28 and pump 36 in the system 10 to fill low-volume containers, the syringe pump 200 may also be used (in whole or in part) in place of the syringe 30 and pump 38, with the valves 232, 236 corresponding to the valves 86, 88.

As an alternative to replacement of syringe 28/syringe pump 36 and/or syringe 30/syringe pump 38, the syringe pump 200 may be connected to the system 10 illustrated in FIGS. 1 and 2 in place of the container 24. For example, the valve 232 may be coupled, so as to be permanently attached to or to be removably detachable from the outlet 66. One or more containers may then be detachably coupled to the valve 236, the operation of the syringe pump 200 causing the one or more containers to be filled with a cell product obtained from the system 10. According to such an embodiment, the syringe pump 200 may be coupled to and operated by the controller 40, or the syringe pump 200 may be coupled to and operated by separate controller. The separate controller, like the controller 40, may include a microprocessor (which, in fact may include multiple physical and/or virtual processors). According to other embodiments, the separate controller may include one or more electrical circuits designed to carry out the actions described herein. In fact, the separate controller may include a microprocessor and other circuits or circuitry. In addition, the separate controller may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described above relative to the syringe pump 200.

Another embodiment of a syringe/syringe pump 300 that may be incorporated into or used in conjunction with the system 10 is illustrated in FIGS. 22-30. According to this embodiment, one or more syringes are filled directly and then detached from the syringe pump 300, which syringes may be intended for storage, shipment, and ultimately use. Thus, these syringes may be delivery containers, and specifically single-use containers. The syringes also may be referred to as pre-filled syringes, in that there is no need to fill the syringes from another container at the time of use.

Figure 22:
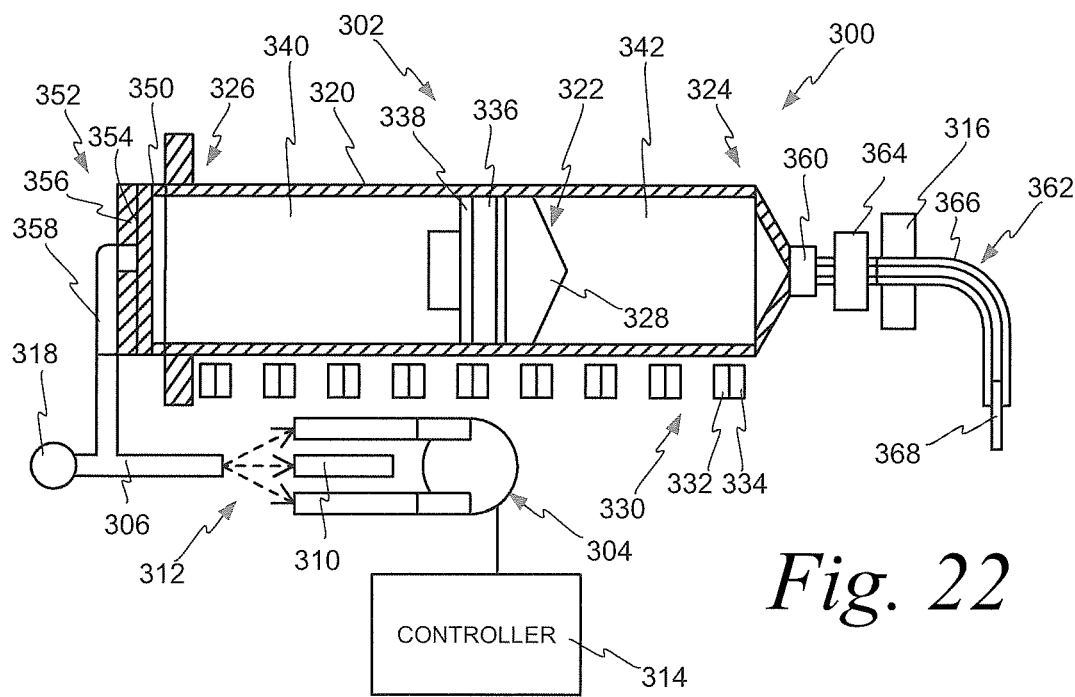
FIG. 22 is a partial schematic diagram of another embodiment of a syringe/syringe pump for producing a pre-filled syringe, which embodiment may be used with a product container such as may be produced in accordance with the embodiment of FIGS. 1-6.
Figure 23:
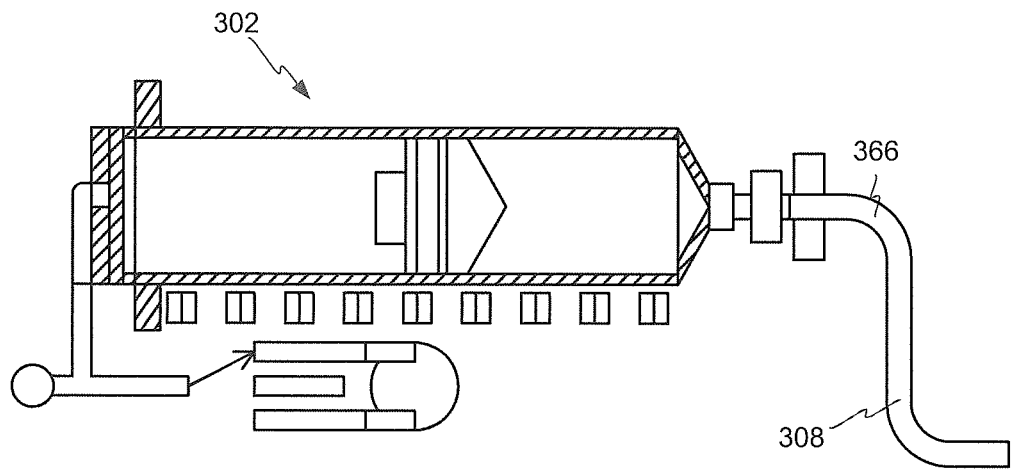
FIGS. 23-28 are partial schematic diagrams of different operational states or positions of the embodiment of FIG. 22.

FIG. 22 illustrates the combination of syringe/syringe pump 300 (referred to simply as syringe pump 300 for ease of explanation). The syringe pump 300 includes a syringe 302, a vacuum/pressure pump 304, a line (e.g. tubing) 306 that connects the pump 304 to one end of the syringe 302, a line (e.g. tubing) 308 (see FIG. 23) that connects the syringe 302 to the system 10 for example, a vent 310, and a valve assembly 312 (which may include one or more valves) to selectively connect the line 306 to the pump 304 and the vent 310. The filling system 300 also includes a controller 314 (which may be the controller 40 according to certain embodiments, and to which the comments made above relative to controller 40 may also apply), which controller 314 is coupled to the pump 304 and may be coupled to other elements as well. For example, the controller may be coupled to the valve assembly 312, a sensor 316 (for example an air or fluid sensor), and a sensor 318 (for example a pressure sensor to sense the driving pressure/vacuum applied by the pump 304 and to provide feedback to the controller 314). The pump 304 and the controller 314 may be associated with a plurality of syringes 302, of which one is illustrated in FIGS. 22-28. While the syringe 302 is illustrated as horizontal in FIGS. 22-28, the syringe 302 may be vertically oriented in actual operation of the system 300, as noted below.

The syringe 302 includes a syringe barrel 320 (which may be made of cyclic olefin copolymer, or other materials such as may be inert, optically clear and, for certain applications, liquid-nitrogen compatible) and a piston or plunger head assembly 322. The plunger head assembly 322 is moveable (translatable) between a first end 324 of the barrel 320 and a second end 326 of the barrel 320. The plunger head assembly 322 includes the plunger 328 and one part of a position detector 330. According to the illustrated embodiment, the position detector 330 also includes a plurality of transmitter/sensor pairs 332, 334. According to the illustrated embodiment, the transmitters (or emitters) 332 may be in the form of infrared light emitting diodes, and the sensors 334 may be in the form of infrared sensors. The transmitter/sensor pairs 332, 334 are disposed along the length of the barrel 322 between the first end 324 and the second end 326. The pairs 332, 334 operate in conjunction with an infrared reflector 336 that is part of the plunger head assembly 322. As one example, the reflector 336 may be in the form of a reflective strip that is disposed about the perimeter of a rigid disc 338 that is attached opposite the plunger 328. The disc 338 may also assist in maintaining the coaxial alignment of the plunger assembly 322 within the barrel 320.

In operation, the position detector 330 (coupled to the controller 314) would use the interaction between the transmitter/sensor pairs 332, 334 and the reflector 336 to determine the positon of the plunger head assembly 322 along the barrel 320. In particular, light emitted from the transmitter 332 would be received by the sensor 334 (or would be received over a threshold amount) if the light contacts the reflector 336. Otherwise, the light would not be received by the sensor 334 (or would not be received below the threshold amount). Depending on the amount of light received by the sensor 334, a signal generated by the sensor 334 would vary (see, e.g., FIG. 21). Depending on the signals received from the individual transmitter/sensor pairs 332, 334, the controller 314 may determine the position of the plunger head assembly 322 along the barrel 320 between the first and second ends 324, 326.

As mentioned above, the pump 304 is attached via line 306 to the syringe 302, and more particularly to the end 326 of the barrel 320. The end 326 is otherwise closed, forming a first variable volume space 340 between the closed end 326 of the barrel 320 and the plunger head assembly 322. Filtered air may be pumped into and out of the space 340 to move the plunger head assembly 322 between the first and second ends 324, 326 of the barrel 320. According to embodiments where the syringe pump 300 is used in conjunction with the system 10, the vacuum/pressure source instead may permit the plunger head assembly 322 to move in response to the action of the syringe 28/syringe pump 36 pushing fluid into the barrel 320, by venting the space 340, for example. The movement of the plunger head assembly 322 causes a second variable volume space 342 to open between the plunger head assembly 322 and the first end 324 and the first end 324 to receive fluid (e.g., a cell product) into the barrel 320. Fluid may be drawn into (or may enter into) the space 342 according to the movement of the plunger head assembly 322.

The syringe 302 may include an aperture 350 at the second end 326, and a filter assembly 352 may include a first connector 354 that permits the filter assembly 352 to be connected to the second end 326 in the aperture 350. According to one embodiment, the first connector 354 may be an o-ring that is received within the aperture 350 to connect the filter assembly 352 to the syringe 302. According to other embodiments, the aperture 350 may be threaded on an inner surface, the first connector 354 may be similarly threaded on an outer surface, and the threaded surfaces may mate to connect the filter assembly 352 to the syringe 302. The filter assembly 352 may also include a filter 356 and a second connector 358 for connection with the line 306. The filter 356 may be a 0.2 µm polytetrafluoroethylene (PTFE) hydrophobic sterile filter. According to one embodiment, the second connector 358 may include an o-ring disposed within a passage, the o-ring receiving an end of the line 306 therethrough to connect the filter assembly 352 to the line 306. According to other embodiments, the second connector 358 may be a female luer slip, for example. The filter assembly 352 closes the end 326 of the barrel 320 and filters the air passing into the space 340.

The syringe 302 may also include a male luer-lock tip 360. Attached to the tip 360 is an assembly 362 that permits the syringe 302 to be connected to a fluid pathway, for example. The assembly 362 includes a female luer-lock connector 364 that may be connected to the male luer-lock tip 360, a section of weldable tubing 366 connected at a first end to the connector 364, and a sealing plug 368 received within a second end of the weldable tubing 366.

In operation, the system 300 may perform an integrity check on the syringe as illustrated in FIG. 22. The controller 314 operates the pump 304 to pump pressurized air into space 340. The controller 314 determines if the position detector 330 indicates that the position of the plunger head assembly 322 has moved. The controller 314 may also determine if other sensors, such as a pressure sensor, indicate that the pressure of the air in the space 340 has changed. If the controller 314 determines that the plunger head assembly 322 has not moved and that the pressure in the space 340 has not changed, the system 300 may begin a method to fill the syringe 302.

The method begins with the attachment of the tubing 366 to the system 10, such by sterile welding tubing 308, 366. See FIG. 23. The controller 314 then operates the pump 304 to move the plunger assembly 322 to the end 324 of the barrel 320, by pumping air into the space 340. See FIG. 24. This may be referred to as the home position. Air in the space 342 is transferred to the system 10, or at least to the tubing 308, 366.

Figure 24:
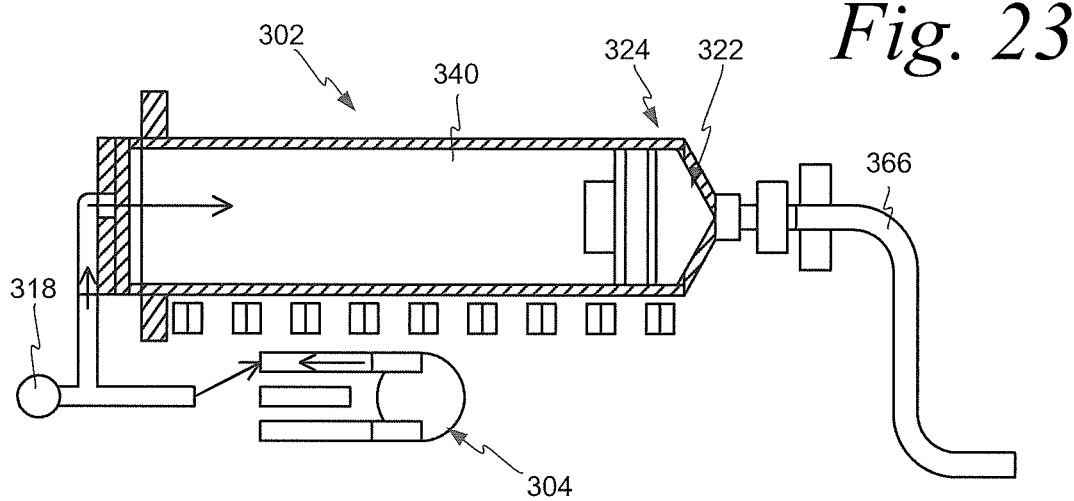
Figure 25:
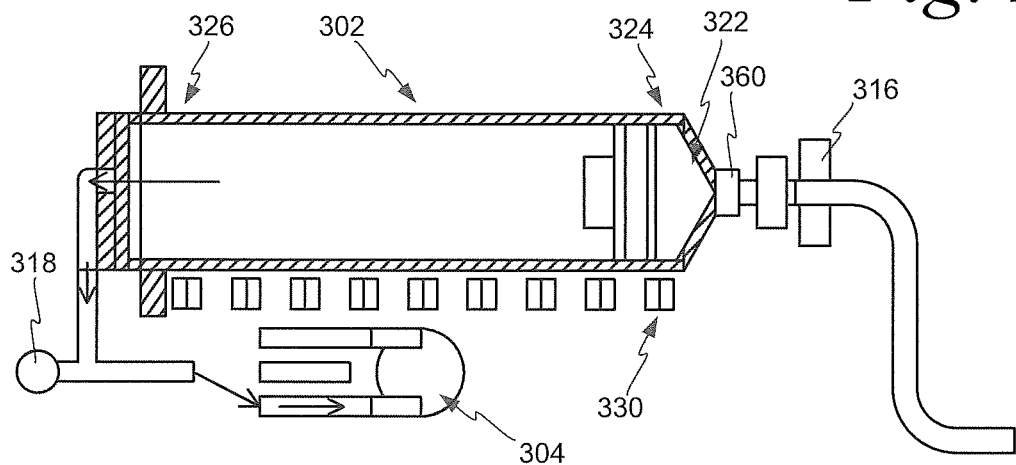
Figure 26:
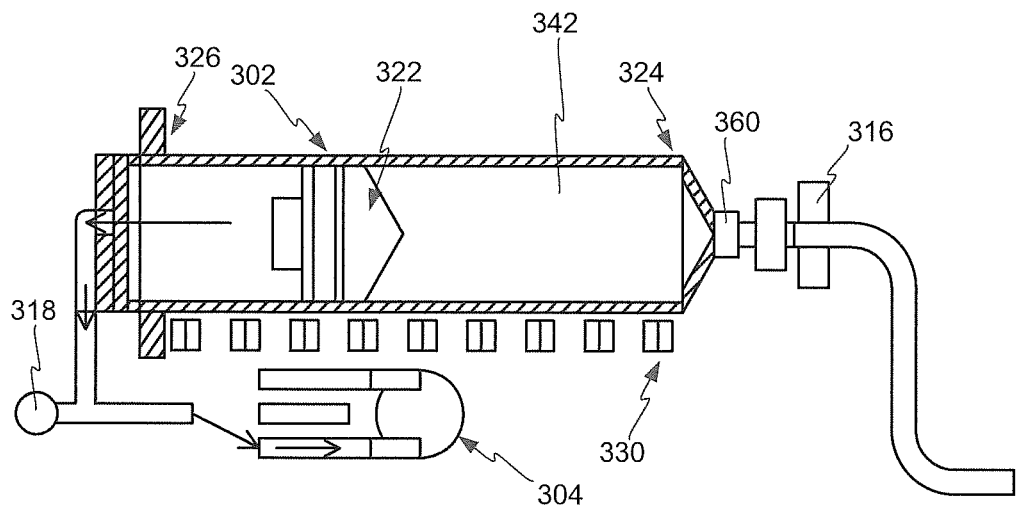
Figure 27:
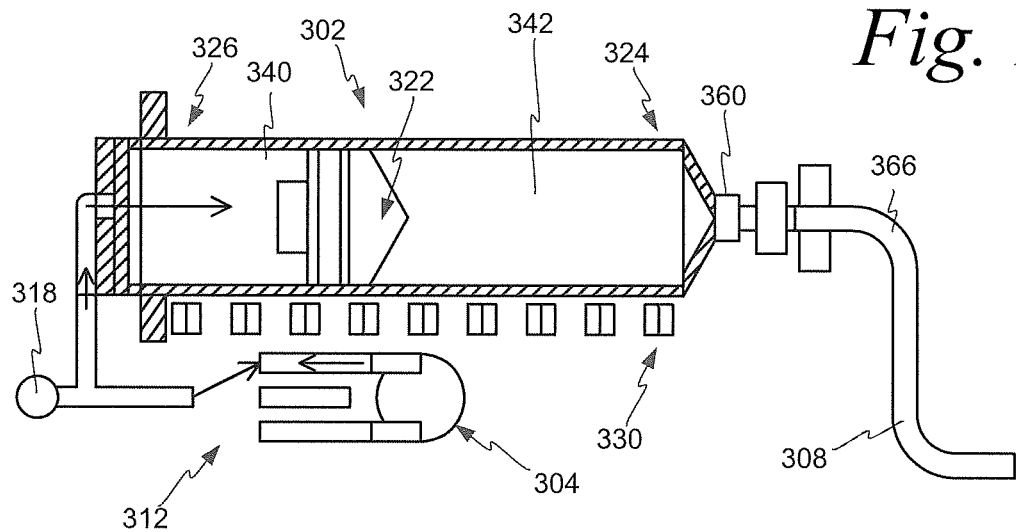
Figure 28:
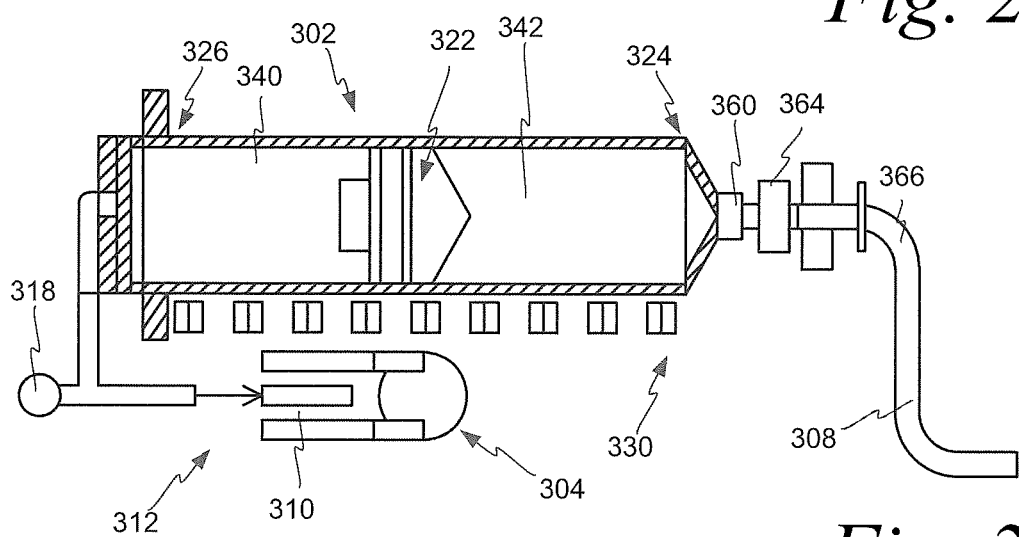

The method then continues with the controller 314 operating the pump 304 to pull a vacuum (see FIG. 25), which causes the plunger head assembly 322 to move from the position (home positon) illustrated in FIG. 24 where the plunger head assembly 322 is near the first end 324 to a position as is illustrated in FIG. 26, wherein the plunger head assembly 322 is nearer the second end 326. Initially, the movement of the plunger head assembly 322 may cause air to enter the space 342. The controller 314 may use the fluid sensor 316 to determine when the fluid enters the tip 360 of the syringe and the position detector 330 to determine the volume of air that will later need to be purged from the syringe 302. This volume may be referred to as the tare volume.

The method continues with the controller 314 operating the pump 304 to move the plunger head assembly 322 to draw a volume into the space 342 that may be equal to the desired volume of fluid from the container 150 that is to be filled into the syringe 302 (which may be referred to as the fill volume) and the volume of air initially drawn into the syringe 302 at the beginning of the method (i.e., the tare volume). The volume that is the sum of the fill volume and the tare volume may be referred to as the stop volume. See FIG. 26.

At this point, it may be desirable to remove the air that remains in the syringe 302. The syringe 302 may be oriented such that the tip 360 is vertical to allow the air to move in the direction of the tip 360. The controller 314 then operates the pump 304 to move the plunger head assembly 322 in the direction of the first end 324, thereby purging the air out of the space 342 into the line 366 in the direction of the system 10. See FIG. 27. The controller 314 determines when the fluid in the space 342 reaches the tip 360, and then ceases operation of the pump 304 and vents the space 340 via the valve assembly 312 and the vent 310. See FIG. 28.

At this point, the syringe 302 is filled. The tubing 366 is heat sealed at the proximal end of the tubing 366, and the remainder of the tubing 366 is removed. The female luer-lock 364 remains connected to the tip 360 to cap the tip 360. The filter assembly 352 is removed from the syringe 302 by unscrewing the filter assembly 352 from the threaded aperture 350 at the second end 326 of the syringe 302. A closed cap 380 is screwed into the threaded aperture 350 to complete the final assembly. See FIG. 29. The luer-lock 364 and the cap 380 are intended to remain in place during shipment and/or storage to preserve the sterile condition of the fluid. The syringe 302 may then be subjected to additional processes, such as freezing.

At the time of use, the syringe 302 is prepared for use, for example by thawing the syringe 302 (where necessary) and by removing the closed cap 380. The disc 338 that is part of the plunger head assembly 322 has a threaded connection hub 382. A threaded first end 384 of a plunger handle 386 is screwed into the threaded connection hub 382, and the syringe 302 is ready for administration once the female luer-lock/cap 364 is removed. See FIG. 30.

As will be recognized, while the syringe pump 300 has been described as used in conjunction with the system 10, in place of the container 24 and connected to the outlet 66, it is possible to replace the syringe 28 and syringe pump 36 with the syringe pump 300. The operation of the syringe pump 300 may be generally as described above relative to system 10 with respect to syringe 28 and pump 36, except that one instance of the syringe 302 of the syringe pump 300 may be filled directly from the fluid pathway 62, and then removed from the syringe pump 300 and replaced with another instance of the syringe 302. The process of filling, removing, and replacing specific instances of the syringe 302 may then be repeated until all of the cell product has been transferred from the system 10. It may even be the case that the first syringe 302, which is used mainly in the early processing steps of the system 10 may be discarded prior to filling the instances of the syringe 302 with cell product from the spinning membrane separator 16.

Thus, an improved method and system for processing (e.g., washing) small volumes of biological cells has been disclosed, in conjunction with an improved method and system for filling low-volume containers with the small volumes of processed. The description provided above, and the other aspects provided below, are intended for illustrative purposes, and are not intended to limit the scope of the disclosure to any particular method, system, apparatus or device described herein.

Other Aspects

Aspect 1. A system for processing fluids and filling a container with a product, the system comprising:

a disposable fluid circuit comprising:
    a spinning membrane separator having an inlet, a retentate outlet, and a filtrate outlet;
    a filtrate container;
    a wash medium container;
    first and second syringes; and
    a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet, a first outlet, and a second outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and reusable hardware configured to accept the disposable fluid circuit and comprising:
    a drive coupled to the spinning membrane separator;
    first and second syringe pumps, the first and second syringes coupled to the first and second syringe pumps respectively, the first syringe pump configured to move a plunger within the first syringe and the second syringe pump configured to move a plunger within the second syringe,
    a third syringe pump with a third syringe having a barrel and a plunger moveable along the barrel between a first end coupled to the first outlet of the second fluid flow path and a second end, the second end being coupled to a vacuum/pressure source with a filter disposed between the second end and the vacuum/pressure source, and the third syringe pump including a position detector to determine the position of the plunger along the barrel of the third syringe; and
    at least one controller coupled to the flow control cassette, the drive, and the first, second, and third syringe pumps, and configured to selectively operate the flow control cassette, the drive and the first, second, and third syringe pumps,
    wherein the at least one controller is configured to operate the vacuum/pressure source to cause or permit the plunger of the third syringe to move to receive a cell product into the barrel of the third syringe.

Aspect 2. The system of aspect 1, wherein the at least one controller is configured to operate the vacuum/pressure source to cause the plunger of the third syringe to move to draw the cell product into the barrel of the third syringe.

Aspect 3. The system of aspect 1 or 2, wherein the at least one controller is configured to operate the vacuum/pressure source to move the plunger of the third syringe to deliver the cell product from the barrel of the third syringe to a container in fluid communication with the third syringe, the container comprising a low-volume container.

Aspect 4. The system of aspect 3, wherein the low-volume container comprises a single-use syringe.

Aspect 5. The system of aspect 1 or 2, wherein the third syringe is detachable from the third syringe pump.

Aspect 6. The system of aspect 5, wherein the third syringe comprises a single-use container.

Aspect 7. The system of any one of aspects 1-6, wherein the flow control cassette comprises at least one fluid interface detector associated with each of the first, second and third fluid pathways.

Aspect 8. The system of any one of aspects 1-7, wherein at least one valve is associated with each of the first inlet and second inlet of the first fluid pathway, the inlet and first outlet of the second fluid flow pathway, and the inlet and first outlet of the third fluid pathway.

Aspect 9. The system of any one of aspects 1-8, wherein each of the first and second syringes comprises a plunger and a body having a discharge port, each syringe being removably secured directly to the housing of the cassette by the discharge port.

Aspect 10. A system for processing fluids and filling a container with a product, the system comprising:
  a disposable fluid circuit comprising:
    a spinning membrane separator having an inlet, a retentate outlet, and a filtrate outlet;
    a filtrate container;
    a wash medium container;
    first and second syringes; and
    a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet, a first outlet, and a second outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and
  reusable hardware configured to accept the disposable fluid circuit and comprising:
    a drive coupled to the spinning membrane separator;
    first and second syringe pumps, the first and second syringes coupled to the first and second syringe pumps respectively, the first syringe pump configured to move a plunger within the first syringe and the second syringe pump configured to move a plunger within the second syringe,
    the first syringe having a barrel and a first plunger moveable along the barrel between a first end coupled to the second outlet of the second fluid flow path and a second end, the second end being coupled to a vacuum/pressure source with a filter disposed between the second end and the vacuum/pressure source, and the first syringe pump including a position detector to determine the position of the first plunger along the barrel; and
    a controller coupled to the flow control cassette, the drive, and the first and second syringe pumps, and configured to selectively operate the flow control cassette, the drive and the first and second syringe pumps,
    wherein the controller is configured to operate the vacuum/pressure source to move the first plunger to draw a cell product into the barrel and to deliver the cell product from the barrel to a container in fluid communication with the first outlet of the second fluid pathway, the container comprising a low-volume container.

Aspect 11. The system of aspect 10, wherein the low-volume container comprises a single-use syringe.

Aspect 12. The system of aspect 11, wherein the low-volume container is detachable from the first outlet of the second fluid pathway.

Aspect 13. A system for processing fluids and filling a container with a product, the system comprising:
  a disposable fluid circuit comprising:
    a spinning membrane separator having an inlet, a retentate outlet, and a filtrate outlet;
    a filtrate container;
    a wash medium container;
    first and second syringes; and
    a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet and an outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and
  reusable hardware configured to accept the disposable fluid circuit and comprising:
    a drive coupled to the spinning membrane separator;
    first and second syringe pumps, the first and second syringes coupled to the first and second syringe pumps respectively, the first syringe pump configured to move a plunger within the first syringe and the second syringe pump configured to move a plunger within the second syringe,
    the first syringe having a barrel and a first plunger moveable along the barrel between a first end coupled to the outlet of the second fluid flow path and a second end, the second end being coupled to a vacuum/pressure source with a filter disposed between the second end and the vacuum/pressure source, and the first syringe pump including a position detector to determine the position of the first plunger along the barrel; and
    a controller coupled to the flow control cassette, the drive, and the first and second syringe pumps, and configured to selectively operate the flow control cassette, the drive and the first and second syringe pumps,
    wherein the controller is configured to operate the vacuum/pressure source to move the first plunger to draw a cell product into the barrel, the first syringe being detachable from the first syringe pump and the outlet of the second fluid pathway.

Aspect 14. The system of aspect 13, wherein the first syringe comprises a low-volume container.

Aspect 15. The system of aspect 14, wherein the first syringe comprises a single-use syringe.

The invention claimed is:
1. A system for processing fluids and filling a container with a product, the system comprising:

a disposable fluid circuit comprising:
  a spinning membrane separator having an inlet, a retentate outlet, and a filtrate outlet;
  a filtrate container;
  a wash medium container;
  first and second syringes; and
  a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet, a first outlet, and a second outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and
reusable hardware configured to accept the disposable fluid circuit and comprising:
a drive coupled to the spinning membrane separator;
first and second syringe pumps, the first and second syringes coupled to the first and second syringe pumps respectively, the first syringe pump configured to move a plunger within the first syringe and the second syringe pump configured to move a plunger within the second syringe,
a third syringe pump with a third syringe having a barrel and a plunger moveable along the barrel between a first end coupled to the first outlet of the second fluid flow path and a second end, the second end being coupled to a vacuum/pressure source with a filter disposed between the second end and the vacuum/pressure source, and the third syringe pump including a position detector to determine a position of the plunger along the barrel of the third syringe; and
at least one controller coupled to the flow control cassette, the drive, and the first, second, and third syringe pumps, and configured to selectively operate the flow control cassette, the drive and the first, second, and third syringe pumps,
wherein the at least one controller is configured to operate the vacuum/pressure source to cause or permit the plunger of the third syringe to move to receive a cell product into the barrel of the third syringe.

2. The system of claim 1, wherein the at least one controller is configured to operate the vacuum/pressure source to cause the plunger of the third syringe to move to draw the cell product into the barrel of the third syringe.

3. The system of claim 1, wherein the at least one controller is configured to operate the vacuum/pressure source to move the plunger of the third syringe to deliver the cell product from the barrel of the third syringe to a container in fluid communication with the third syringe, the container comprising a low-volume container.

4. The system of claim 3, wherein the low-volume container comprises a single-use syringe.

5. The system of claim 1, wherein the third syringe is detachable from the third syringe pump.

6. The system of claim 5, wherein the third syringe comprises a single-use container.

7. The system of claim 1, wherein the flow control cassette comprises at least one fluid interface detector associated with each of the first, second and third fluid pathways.

8. The system of claim 1, wherein at least one valve is associated with each of the first inlet and second inlet of the first fluid pathway, the inlet and first outlet of the second fluid flow pathway, and the inlet and first outlet of the third fluid pathway.

9. The system of claim 1, wherein each of the first and second syringes comprises a plunger and a body having a discharge port, each syringe being removably secured directly to the housing of the cassette by the discharge port.

10. A system for processing fluids and filling a container with a product, the system comprising:
a disposable fluid circuit comprising:
  a spinning membrane separator having an inlet, a retentate outlet, and a filtrate outlet;
  a filtrate container;
  a wash medium container;
  first and second syringes; and
  a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet, a first outlet, and a second outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and
reusable hardware configured to accept the disposable fluid circuit and comprising:
  a drive coupled to the spinning membrane separator;
  first and second syringe pumps, the first and second syringes coupled to the first and second syringe pumps respectively, the first syringe pump configured to move a plunger within the first syringe and the second syringe pump configured to move a plunger within the second syringe,
  the first syringe having a barrel and a first plunger moveable along the barrel between a first end coupled to the second outlet of the second fluid flow path and a second end, the second end being coupled to a vacuum/pressure source with a filter disposed between the second end and the vacuum/pressure source, and the first syringe pump including a position detector to determine a position of the first plunger along the barrel; and
  a controller coupled to the flow control cassette, the drive, and the first and second syringe pumps, and configured to selectively operate the flow control cassette, the drive and the first and second syringe pumps,
  wherein the controller is configured to operate the vacuum/pressure source to move the first plunger to draw a cell product into the barrel and to deliver the cell product from the barrel to a container in fluid communication with the first outlet of the second fluid pathway, the container comprising a low-volume container.

11. The system of claim 10, wherein the low-volume container comprises a single-use syringe.

12. The system of claim 11, wherein the low-volume container is detachable from the first outlet of the second fluid pathway.

13. A system for processing fluids and filling a container with a product, the system comprising:
- a disposable fluid circuit comprising:
  - a spinning membrane separator having an inlet, a retentate outlet, and a filtrate outlet;
  - a filtrate container;
  - a wash medium container;
  - first and second syringes; and
  - a flow control cassette comprising a housing and (i) a first fluid pathway with a first inlet configured to be in fluid communication with a source container, a second inlet in fluid communication with the wash medium container, and an outlet in fluid communication with the inlet of the spinning membrane separator; (ii) a second fluid pathway with an inlet in fluid communication with the retentate outlet and an outlet in fluid communication with the first syringe; (iii) a third fluid pathway with an inlet in fluid communication with the filtrate outlet, a first outlet in fluid communication with the filtrate container, and a second outlet in fluid communication with the second syringe; and at least one valve associated with each of the first, second and third fluid pathways; and
- reusable hardware configured to accept the disposable fluid circuit and comprising:
  - a drive coupled to the spinning membrane separator;
  - first and second syringe pumps, the first and second syringes coupled to the first and second syringe pumps respectively, the first syringe pump configured to move a plunger within the first syringe and the second syringe pump configured to move a plunger within the second syringe,
  - the first syringe having a barrel and a first plunger moveable along the barrel between a first end coupled to the outlet of the second fluid flow path and a second end, the second end being coupled to a vacuum/pressure source with a filter disposed between the second end and the vacuum/pressure source, and the first syringe pump including a position detector to determine a position of the first plunger along the barrel; and
  - a controller coupled to the flow control cassette, the drive, and the first and second syringe pumps, and configured to selectively operate the flow control cassette, the drive and the first and second syringe pumps,
  - wherein the controller is configured to operate the vacuum/pressure source to move the first plunger to draw a cell product into the barrel, the first syringe being detachable from the first syringe pump and the outlet of the second fluid pathway.

14. The system of claim 13, wherein the first syringe comprises a low-volume container.

15. The system of claim 14, wherein the first syringe comprises a single-use syringe.

* * * * *